United States Patent
Iguchi et al.

(10) Patent No.: US 10,463,875 B2
(45) Date of Patent: *Nov. 5, 2019

(54) LIGHT IRRADIATION SUBSTRATE

(71) Applicant: SHARP KABUSHIKI KAISHA, Sakai, Osaka (JP)

(72) Inventors: Katsuji Iguchi, Sakai (JP); Hidenori Kawanishi, Sakai (JP); Jun Mori, Sakai (JP); Tohru Nakanishi, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 27 days.

This patent is subject to a terminal disclaimer.

(21) Appl. No.: 15/553,860

(22) PCT Filed: Jan. 22, 2016

(86) PCT No.: PCT/JP2016/051883
§ 371 (c)(1),
(2) Date: Aug. 25, 2017

(87) PCT Pub. No.: WO2016/136345
PCT Pub. Date: Sep. 1, 2016

(65) Prior Publication Data
US 2018/0043178 A1 Feb. 15, 2018

(30) Foreign Application Priority Data
Feb. 26, 2015 (JP) .................. 2015-036926

(51) Int. Cl.
*A61N 5/06* (2006.01)

(52) U.S. Cl.
CPC .......... *A61N 5/0616* (2013.01); *A61N 5/062* (2013.01); *A61N 2005/063* (2013.01); *A61N 2005/0645* (2013.01); *A61N 2005/0652* (2013.01)

(58) Field of Classification Search
None
See application file for complete search history.

(56) References Cited

U.S. PATENT DOCUMENTS

| 5,616,140 A | 4/1997 | Prescott |
| 5,913,883 A | 6/1999 | Alexander et al. |

(Continued)

FOREIGN PATENT DOCUMENTS

| JP | 2011-210705 A | 10/2011 |
| JP | 2012-84392 A | 4/2012 |

(Continued)

OTHER PUBLICATIONS

Kuniyuki Morimoto, et al., 'Photodynamic Therapy Using Systemic Administration of 5-Aminolevulinic Acid and a 410-nm Wavelength Light-Emitting Diode for Methicillin-Resistant *Staphylococcus aureus*-Infected Ulcers in Mice', PLOS ONE, Aug. 2014, vol. 9, Issue 8 e105173.

*Primary Examiner* — Carl H Layno
*Assistant Examiner* — Manolis Pahakis
(74) *Attorney, Agent, or Firm* — ScienBiziP, P.C.

(57) ABSTRACT

A light irradiation substrate includes plural unit substrates that have a flexible substrate. A portion of the unit substrates have a pair of external connection portions. A first surface of the flexible substrate is provided with an LED chip and a wire for each of the unit substrates, and a second surface is provided with a back surface wire across the unit substrates.

5 Claims, 10 Drawing Sheets

(56) References Cited

U.S. PATENT DOCUMENTS

| | | | |
|---|---|---|---|
| 6,290,713 B1 | 9/2001 | Russell | |
| 6,459,919 B1* | 10/2002 | Lys | A61N 5/0616 |
| | | | 315/291 |
| 6,596,016 B1* | 7/2003 | Vreman | A61N 5/0621 |
| | | | 128/903 |
| 8,097,926 B2* | 1/2012 | De Graff | H01L 27/14687 |
| | | | 257/419 |
| 8,886,334 B2* | 11/2014 | Ghaffari | A61B 1/00082 |
| | | | 607/115 |
| 9,289,132 B2* | 3/2016 | Ghaffari | A61B 1/00082 |
| 2005/0104059 A1* | 5/2005 | Friedman | A61M 25/1011 |
| | | | 257/40 |
| 2005/0116667 A1* | 6/2005 | Mueller | E04F 13/08 |
| | | | 315/312 |
| 2007/0208396 A1* | 9/2007 | Whatcott | A61N 5/0613 |
| | | | 607/88 |
| 2008/0042558 A1* | 2/2008 | Buchhauser | H01L 27/3225 |
| | | | 313/504 |
| 2008/0269849 A1* | 10/2008 | Lewis | A61N 5/0613 |
| | | | 607/91 |
| 2009/0018622 A1* | 1/2009 | Asvadi | A61N 5/0621 |
| | | | 607/91 |
| 2010/0045175 A1* | 2/2010 | Mathai | H01L 27/3209 |
| | | | 313/504 |
| 2010/0045189 A1* | 2/2010 | Storch | H01L 51/50 |
| | | | 315/149 |
| 2010/0076527 A1* | 3/2010 | Hammond | G09F 9/33 |
| | | | 607/88 |
| 2010/0106077 A1 | 4/2010 | Rabin et al. | |
| 2010/0259928 A1* | 10/2010 | Ou Yang | F21K 9/00 |
| | | | 362/235 |
| 2011/0181494 A1* | 7/2011 | Wong | G09F 9/33 |
| | | | 345/1.3 |
| 2011/0181495 A1* | 7/2011 | Chu | G09F 9/33 |
| | | | 345/1.3 |
| 2011/0195532 A1* | 8/2011 | Lerman | H01L 25/0753 |
| | | | 438/27 |
| 2011/0222286 A1 | 9/2011 | Oba et al. | |
| 2011/0242771 A1* | 10/2011 | Bhattacharya | H05K 1/038 |
| | | | 361/733 |
| 2012/0165759 A1* | 6/2012 | Rogers | A61B 5/6867 |
| | | | 604/264 |
| 2012/0253433 A1* | 10/2012 | Rosen | A61N 5/0621 |
| | | | 607/91 |
| 2012/0320581 A1* | 12/2012 | Rogers | H01L 24/24 |
| | | | 362/235 |
| 2013/0144364 A1 | 6/2013 | Wagenaar et al. | |
| 2013/0258662 A1* | 10/2013 | Treanton | F21S 2/005 |
| | | | 362/235 |
| 2013/0301264 A1* | 11/2013 | Van Gompel | F21S 2/005 |
| | | | 362/236 |
| 2013/0304019 A1* | 11/2013 | Cooper | A61N 5/062 |
| | | | 604/501 |
| 2014/0207215 A1* | 7/2014 | Fiset | A61N 5/0614 |
| | | | 607/94 |
| 2014/0226329 A1* | 8/2014 | Oraw | H01L 25/0753 |
| | | | 362/235 |
| 2014/0268780 A1* | 9/2014 | Wang | F21V 19/003 |
| | | | 362/249.06 |
| 2015/0188082 A1* | 7/2015 | Rohatgi | H01L 51/5253 |
| | | | 257/40 |
| 2015/0194123 A1* | 7/2015 | Lee | G02B 3/0037 |
| | | | 345/1.3 |
| 2015/0267907 A1* | 9/2015 | Thompson | F21V 23/06 |
| | | | 362/249.06 |
| 2015/0290470 A1* | 10/2015 | Tapper | A61N 5/0616 |
| | | | 607/91 |
| 2016/0076708 A1* | 3/2016 | Shirilla | F21S 2/005 |
| | | | 362/235 |
| 2016/0123569 A1* | 5/2016 | Cummings | F21S 2/005 |
| | | | 362/249.02 |
| 2016/0267836 A1* | 9/2016 | Meersman | G09G 3/32 |
| 2017/0118838 A1* | 4/2017 | Williams | H05K 3/4691 |

FOREIGN PATENT DOCUMENTS

| | | |
|---|---|---|
| JP | 2013-145688 A | 7/2013 |
| WO | 0114012 A1 | 3/2001 |
| WO | 2008144157 A1 | 11/2008 |
| WO | 2012023086 A1 | 2/2012 |

* cited by examiner

LIGHT IRRADIATION SUBSTRATE

TECHNICAL FIELD

The present invention relates to a light irradiation substrate that is used for phototherapy in which mainly an affected part of human or animal skin is irradiated with light and for hairdressing and beauty treatments.

BACKGROUND ART

Phototherapy is used for various purposes such as treatments for diseases such as neonatal jaundice, psoriasis, and acne, pain palliation, and beauty treatments. Green light and blue-white light are used for treatments for neonatal jaundice, ultra-violet light is used for treatments for psoriasis, and blue light, red light, and yellow light are used for treatments for acne. In such a manner, various kinds of light sources are used in accordance with uses.

NPL 1 describes a treatment method for skin ulcer infected with methicillin-resistant *Staphylococcus aureus* (hereinafter referred to as "MRSA"), which uses near ultra-violet light. This treatment method is a therapeutic method in which an infected part with antibiotic resistant *Staphylococcus aureus* is irradiated with near ultra-violet light (at a wavelength of approximately 410 nm) and the bacteria are thereby killed and is based on a process in which systemically administered 5-aminolevulinic acid (hereinafter referred to as "ALA") is metabolized to protoporphyrin IX (hereinafter referred to as "PpIX") and accumulated in the bacteria and the bacteria are destroyed from internal portions of cells or the bacteria by active oxygen which is generated when PpIX is decomposed by near ultra-violet light.

The above treatment method has been considered as a very highly promising technique with a wide application range, which causes no side effect for cells themselves of the affected part but kills antibiotic resistant bacteria without causing antibiotic contamination.

For popularization of such a technique, a light irradiation device is demanded which may perform uniform light irradiation for affected parts with various three-dimensional shapes and sizes.

In related art, as a light irradiation device, for example, devices that use light sources such as an excimer lamp and an arc light, devices that use laser as light sources, devices of a type that performs planar irradiation with treatment light by using optical fibers, and so forth have been known.

However, the above-described related art has the following problems.

For example, in a case of the light sources such as the excimer lamp and the arc light, the affected part is arranged in a specific distance with respect to a fixed light source and is irradiated with the treatment light. However, in a case of using such a lamp type light source, the treatment light fails on other portions than the affected part because the irradiation area is too large. Thus, there is a concern about various side effects for a normal site. Accordingly, some sort of shielding measure for preventing irradiation for the normal site with the treatment light is requested, and a treatment consumes time and labor. For example, in a case where a disease that occurs to a portion of a face, an eye pad (blindfold) for protecting eyes that are normal sites is requested. In addition, in order to protect the normal sites of the face, a mask that only exposes the affected part of the face is also requested. Further, a patient has to keep a still posture for several ten minutes in a state where his/her body is restrained for the treatment. This is not a comfortable experience although the experience is for the treatment. Further, for example, in a case where the affected part has a curved surface as on an arm or a leg, a lamp type irradiation device may force the patient to keep a very difficult posture depending on a site such as a front side, a back side, or a lateral side. Further, the irradiation intensity is different with respect to each position of the affected part in accordance with an angle or a distance between the affected part that has a curved portion and the lamp. Thus, a case may occur where it is difficult to uniformly irradiate the whole affected part with the treatment light. In addition, because a device that uses such a lamp type light source has many accessory devices such as a power source and a cooling device and is large in size, the device requests a large space for installation and is expensive in price. Accordingly, the device may be installed only in a treatment facility, and attendance at the treatment facility is necessary.

Meanwhile, in the device that uses laser as the light source, because the irradiation light is spot light with a small irradiation area, scanning by the spot light is requested so that the whole affected part with a large area is irradiated with the treatment light, and the device becomes complicated and expensive.

Further, because the efficiency of delivering light into the optical fibers is comparatively low, a device of a type that performs planar irradiation with the treatment light by using the optical fibers necessarily has low irradiation power and only fits the treatment for a comparatively long time.

Based on such a background, a flexible substrate is demanded which includes the light source capable of keeping a specific distance from the affected part and of covering the affected part along the shape of the affected part.

For such a desire, several techniques that will be described in the following have been suggested.

For example, PTL 1 discloses a light irradiation device in which laser and light-emitting diodes (LED) as light-emitting light sources are arranged on the flexible substrate and which is used while being wound around the affected part. PTL 2 discloses a light irradiation device for a face in which the LEDs as the light emitting light sources are arranged on the flexible substrate and which is used by covering the face. PTL 3 discloses a light irradiation device with flexibility in which a large number of LEDs serving as the light-emitting light sources are arranged on the flexible substrate and which performs light irradiation by winding the flexible substrate around the affected part. PTL 4 discloses a light irradiation device in which the LEDs serving as the light-emitting light sources are arranged inside a cap on an assumption of application to a head. PTL 5 discloses a light irradiation device in which the LEDs serving as the light-emitting light sources are arranged on the flexible substrate, a light-transmissive substance is interposed between the affected part and the LEDs, and light emitted by the LEDs may thereby be transmitted to the affected part.

Based on PTLs 1 to 5, a flexible base material with flexibility covers the affected part, and the affected part may thereby be covered along the shape of the affected part. Further, the LED is small compared to other light sources and may perform light irradiation for the affected part with a curved surface. In a case where size reduction and weight saving of the light irradiation device are made, it is possible to perform the treatment home. Thus, it is expected that the flexible base material that includes the LEDs covers the affected part and performs light irradiation as described in PTLs 1 to 5, various loads on patients may thereby be alleviated, and the affected part with a curved surface may be irradiated with uniform treatment light.

CITATION LIST

Patent Literature

PTL 1: U.S. Pat. No. 5,616,140 (registered on Apr. 1, 1997)
PTL 2: U.S. Pat. No. 5,913,883 (registered on Jun. 22, 1999)
PTL 3: International Publication No. WO01/14012 Pamphlet (laid open on Mar. 1, 2001)
PTL 4: International Publication No. WO2008/144157 Pamphlet (laid open on Nov. 27, 2008)
PTL 5: International Publication No. WO2012/023086 Pamphlet (laid open on Feb. 23, 2012)

Non Patent Literature

NPL 1: Kuniyuki Morimoto, and six others, "Photodynamic Therapy Using Systemic Administration of 5-Aminolevulinic Acid and a 410-nm Wavelength Light-Emitting Diode for Methicillin-Resistant *Staphylococcus aureus*-Infected Ulcers in Mice", PLOS ONE, August 2014, Volume 9, Issue 8 e105173, (published on Aug. 20, 2014)

SUMMARY OF INVENTION

Technical Problem

However, affected parts as targets to be irradiated with treatment light have various shapes and sizes depending on patients. In addition, the shapes and sizes vary depending on sites. In order to handle the affected parts that have such various shapes and sizes, light irradiation substrates such as flexible substrates that include LEDs have to be fabricated only one by one in a customized manner, and the light irradiation substrate thus becomes very expensive. Further, because fabrication of such a light irradiation substrate is started after confirmation of the shape and size of the affected part, time is consumed until delivery, and a circumstance may occur in which the delivery is too late for an emergency treatment.

On the other hand, in a case of attempting to allow such a light irradiation substrate to be versatile, regardless of whether or not being actually used, a large number of the light irradiation substrates with various sizes including a very large size have to be fabricated. In such a case, the light irradiation substrates that are not actually used are fabricated, production of a large number of wasted substrates is anticipated, and retaining a large number of stocks may not be avoided. This becomes a large load on fabricators, and economical efficiency is hugely lowered.

Thus, a light irradiation substrate is demanded which may suppress costs and handle affected parts which are with various sizes or are not even. Such a light irradiation substrate enables an optimal treatment at minimum requested costs even in an emergency case.

The present invention has been made in consideration of above problems in related art, and an object thereof is to provide a light irradiation substrate that may suppress costs, handle treatments for diseased parts with various sizes, perform substantially uniform light irradiation for an uneven affected part, suppress side effects by light irradiation to a minimum, and realize efficient and uniform light irradiation.

Solution to Problem

To solve the above problems, a light irradiation substrate according to one aspect of the present invention includes plural unit substrates that have a flexible substrate and are mutually detachable, in which a first surface of the flexible substrate has a light-emitting element and a first wire for each of the unit substrates, a portion of the unit substrates among the unit substrates have at least one pair of external connection portions that supply power from an outside to the light-emitting element via the first wire, and a second wire that is connected with the external connection portion and the first wire and supplies power from the external connection portion to the light-emitting element of the unit substrate which is not provided with the external connection portion via the first wire is provided on a second surface on an opposite side to the first surface on the flexible substrate and across the unit substrates.

Advantageous Effects of Invention

One aspect of the present invention may provide a light irradiation substrate that may suppress costs, handle treatments for diseased parts with various sizes, perform substantially uniform light irradiation for an uneven affected part, suppress side effects by light irradiation to a minimum, and realize efficient and uniform light irradiation.

DESCRIPTION OF EMBODIMENTS

Embodiments of the present invention will hereinafter be described in detail. However, dimensions, materials, shapes, relative arrangement, processing methods, and so forth of configuration elements described in the following embodiments are only some embodiments. It should be noted that those are not construed as limiting the scope of the present invention. In addition, the drawings are schematic illustrations, and dimensional ratios and shapes may be different from the reality.

First Embodiment

One embodiment of the present invention will be described in the following based on FIGS. 1 to 6. Note that in the following, a description will be made while a surface on which a light-emitting diode (LED) chip is mounted in a light irradiation substrate is defined as a front surface (first surface) and a surface on the opposite side to the surface on which the LED chip is mounted is defined as a back surface (second surface).

Figure 1:
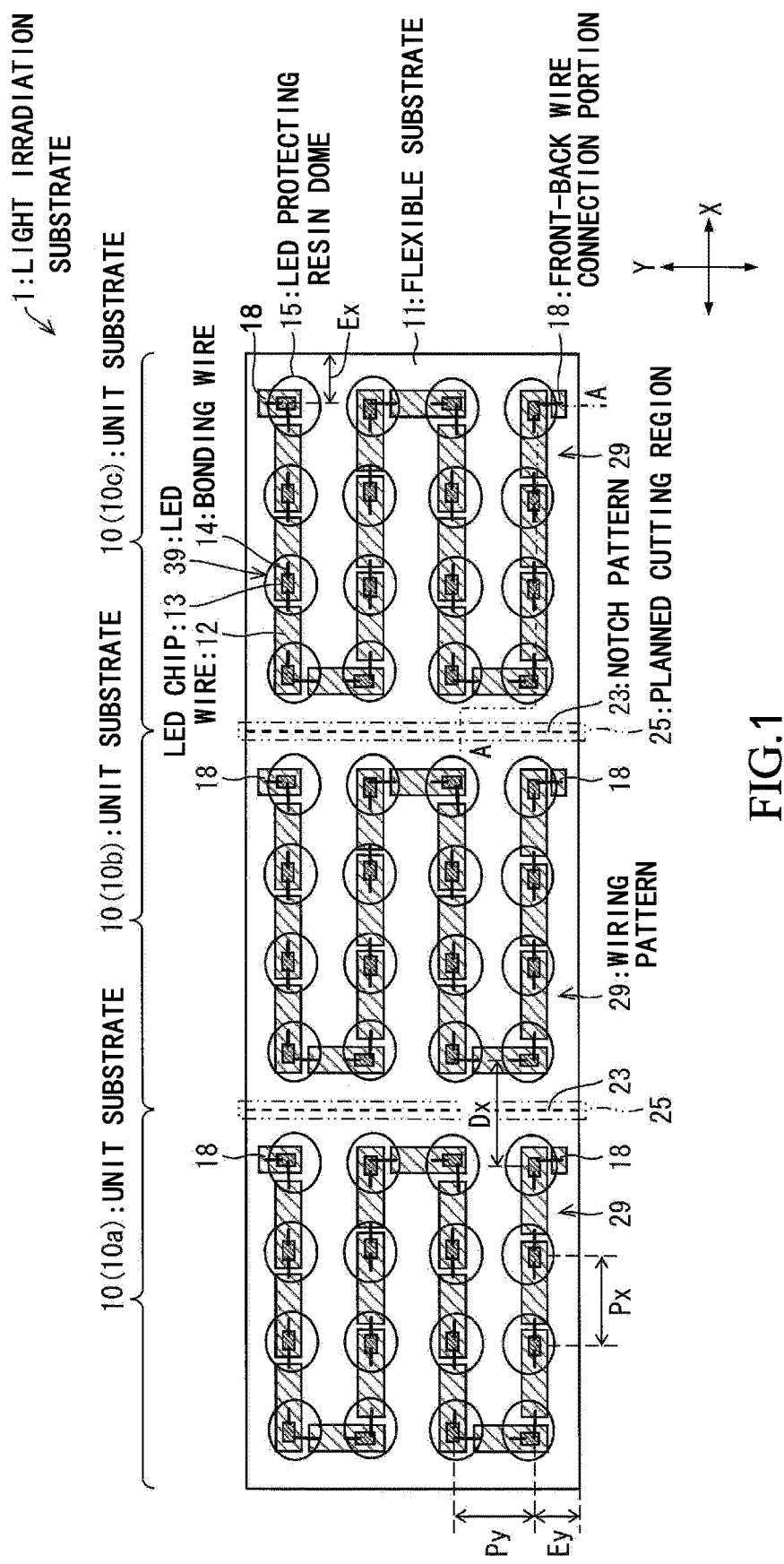
FIG. 1 is a front surface schematic diagram that illustrates a configuration of a light irradiation substrate according to a first embodiment of the present invention.
Figure 2:
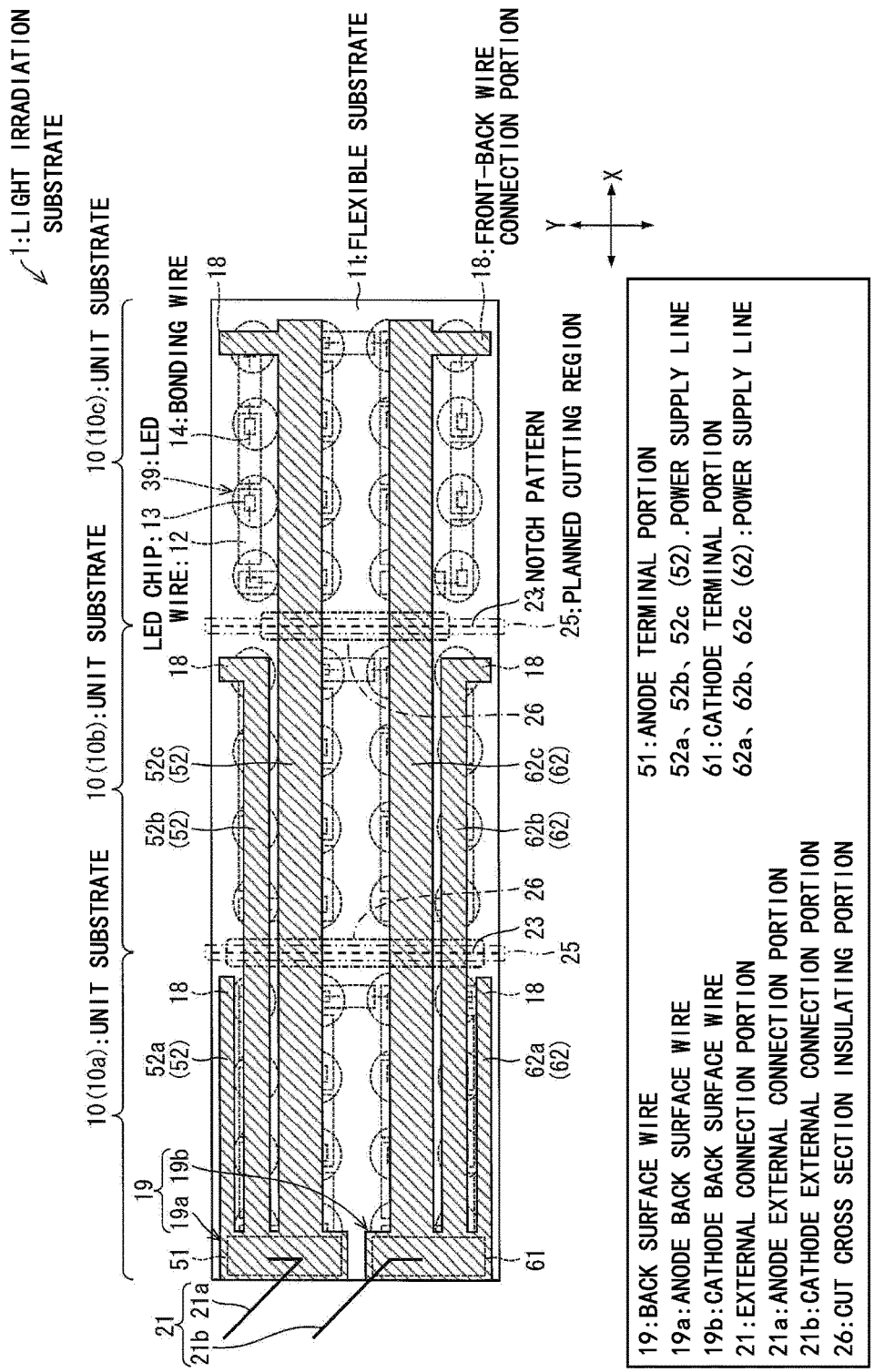
FIG. 2 is a back surface schematic diagram that illustrates the configuration of the light irradiation substrate according to the first embodiment of the present invention.
Figure 3:
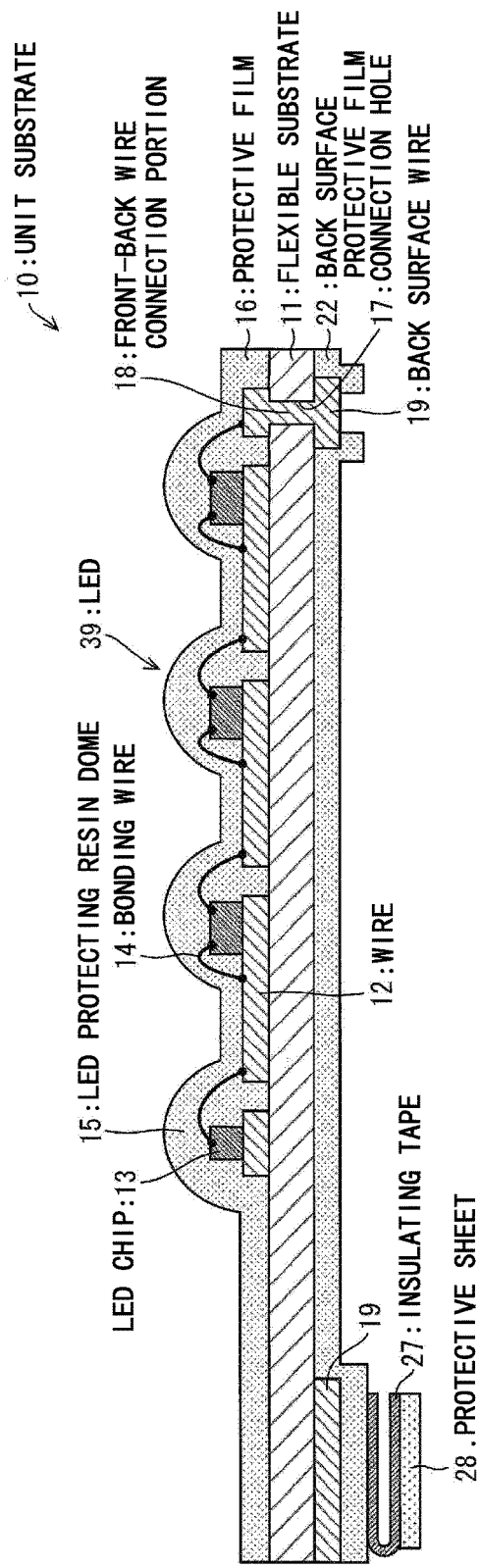
FIG. 3 is a cross-sectional schematic diagram that illustrates a configuration of a unit substrate according to the first embodiment of the present invention.

FIG. 1 is a front surface schematic diagram that illustrates a configuration of a light irradiation substrate 1 according to this embodiment. FIG. 2 is a back surface schematic diagram that illustrates the configuration of the light irradiation substrate 1 according to this embodiment. FIG. 3 is a cross-sectional schematic diagram that illustrates a configuration of a unit substrate according to this embodiment.

Note that FIG. 3 corresponds to an arrow cross-sectional diagram taken along line A-A of the light irradiation substrate 1 illustrated in FIG. 1. However, FIG. 1 does not illustrate a protective film 16 for convenience of illustration.

(Outline Configuration of Light Irradiation Substrate 1)

As illustrated in FIG. 1 and FIG. 2, the light irradiation substrate 1 is configured with plural unit substrates 10 that are mutually detachable.

A boundary portion between the neighboring unit substrates 10 is a planned cutting region 25 for cutting the light irradiation substrate 1. In each of the planned cutting regions 25, a notch pattern 23 for detaching the unit substrate 10 is formed. That is, the unit substrates 10 are connected with each other via the planned cutting region 25.

Note that FIG. 1 and FIG. 2 illustrate a case where the light irradiation substrate 1 includes three unit substrates 10a to 10c as the unit substrates 10, as an example. In a case where those unit substrates 10a to 10c do not have to be particularly distinguished, those unit substrates 10a to 10c will generically and simply be referred to as unit substrate 10.

The irradiation substrate 1 includes a flexible substrate 11, plural wires 12 (first wire), plural LED chips 13 (light-emitting element), plural bonding wires 14, the protective film 16, plural LED protecting resin domes 15, plural connection holes and front-back wire connection portions 18, a back surface wire 19 (second wire), external connection portions 21, a back surface protective film 22, plural insulating tapes 27, plural protective sheets 28, and connection portion seals that are not illustrated.

On one main surface (front surface or first surface) of the flexible substrate 11, the plural wires 12 and the plural LED chips 13 are provided to each of the unit substrates 10. One LED chip 13 is mounted on one wire 12. The LED chip 13 is connected with the wire 12 on which the LED chip 13 is mounted and the wire 12 that neighbors the wire 12 in each of the unit substrates 10 by the bonding wires 14.

The LED chips 13 are arranged on each of the unit substrates 10 as a 4×4 two-dimensional array along an X direction (first direction) and a Y direction (second direction) that is orthogonal to the X direction in the same plane as the X direction.

Here, the X direction and the Y direction are alignment directions of the LED chips 13. In this embodiment, particularly, the alignment direction of the unit substrates 10 illustrated in FIG. 1 and FIG. 2, in other words, an extending direction of power supply lines 52 and 62 in the back surface wire 19 will be referred to as X direction. This embodiment uses the light irradiation substrate 1 of 120 mm×40 mm that has the shape in which three unit substrates 10 of 40 mm-square are lined up in one line. The LED chips 13 are aligned in parallel with each side of each of the unit substrates 10.

The wires 12 in each of the unit substrates 10 are arranged to be lined up such that the respective LED chips 13 mounted on the wires 12 are arranged as the above-described two-dimensional array. The wires 12 in each of the unit substrates 10 are connected to be lined up in one line (that is, in a belt-like manner) by the LED chips 13 and the bonding wires 14.

In this embodiment, the wires 12 on a front side of the flexible substrate 11 are coupled with each other by the LED chips 13 and the bonding wires 14 only in the unit substrate 10 but are not coupled among the other unit substrates 10.

The wires 12 in each of the unit substrates 10 are arranged to meander such that a wiring pattern 29 that is formed with the plural wires 12 connected to be lined up in one line by the LED chips 13 and the bonding wires 14 forms a meandering pattern that curves in a U-shape while facing ends of each of the unit substrates 10.

The wiring pattern 29 in the same shape that is formed with the wires 12 connected by the bonding wires 14 via the LED chips 13 is formed in each of the unit substrates 10. Consequently, in the flexible substrate 11, plural independent wiring patterns 29 that are formed with the plural wires 12 connected with each other by the bonding wires 14 via the LED chips 13 and that are spaced apart from each other are formed repeatedly.

The above wiring pattern 29 formed on each of the unit substrates 10 is provided to be spaced apart from the planned cutting regions 25 of the light irradiation substrate 1 such that the notch pattern 23 is positioned at the center between the neighboring wiring patterns 29.

Note that a sufficient space in which cutting is performed without damaging the wires 12 in each of the unit substrates 10 is preferably provided between the neighboring wiring patterns 29.

The LED chip 13 and the bonding wires 14 are covered by the LED protecting resin dome 15 for the LED chip 13 and the respective bonding wires 14 connected with the LED chip 13. Further, the front surface of the flexible substrate 11 that is not covered by the LED protecting resin domes 15 is covered by the protective film 16 that covers the wires 12.

In this embodiment, as described above, as an LED 39, an LED element in which each of the LED chips 13 is covered by the LED protecting resin dome 15 is used.

Meanwhile, as illustrated in FIG. 2, on the other main surface (back surface or second surface) of the flexible substrate 11, the back surface wire 19 that connects the LED chips 13 on each of the unit substrates 10 in series is formed.

As illustrated in FIG. 3, the flexible substrate 11 is provided with the plural connection holes 17 that pass through the flexible substrate 11. The wire 12 and the back surface wire 19 are connected together via each of the connection holes 17. Each of the connection holes 17 is provided with the front-back wire connection portion 18 that connects the wire 12 and the back surface wire 19 together.

Further, the wire 12 is electrically connected with the external connection portion 21 via the back surface wire 19.

A wire connection portion between the external connection portion 21 and the back surface wire 19 is insulated and separated by the connection portion seal that is not illustrated. Further, a surface of the back surface wire 19 is covered by the back surface protective film 22.

Further, on the back surface protective film 22 on a back surface side of the flexible substrate 11, the adhesive insulating tape 27 that covers a cut cross section of the back surface wire 19 in the light irradiation substrate 1 after detachment of the unnecessary unit substrate 10 is stuck while facing the planned cutting region 25. A portion of an adhesive surface of the insulating tape 27 is covered by the protective sheet 28.

Next, each configuration element in the light irradiation substrate 1 will be described more in detail.

(Flexible Substrate 11)

The flexible substrate 11 is an insulating substrate and is formed of an insulating film such as polyimide, for example. However, the material of the flexible substrate 11 does not have to be limited to polyimide, but any material may be used as long as the material is an insulating material and has requested strength and flexibility.

In this embodiment, as the flexible substrate 11, a film with a size in the X direction and Y direction of 120 mm×40 mm and with a thickness of 50 μm, which corresponds to the size in which three unit substrates of 40 mm-square are lined up, is used. However, the size of the flexible substrate 11 may appropriately be decided in consideration of post-process, and the thickness may appropriately be decided in the range in which insulation, strength, and flexibility may be secured in accordance with materials.

In each of the planned cutting regions 25 in the flexible substrate 11, perforation-like nicks (slits) are formed as the notch pattern 23 for detaching the unit substrate 10, for example.

The notch pattern 23 is formed in the planned cutting region 25 in the flexible substrate 11 as described above. Thus, for example, the flexible substrate 11 is folded at the planned cutting region 25, and the unnecessary unit substrate 10 may thereby be detached without using a separate cutting tool.

Note that the size of the unit substrate 10 is desirably a size that enables light irradiation while covering only an affected part in view of reducing restraint of a patient and suppressing the load on the patient to a minimum. Thus, for example, in consideration of use for a local disease with a comparatively small area, the unit substrate 10 is desirably formed in the size that is correspondent to the local disease.

(Wire 12, Back Surface Wire 19, and External Connection Portion 21)

As described above, the wires 12 are provided on the front surface of the flexible substrate 11, and the back surface wire is provided on the back surface of the flexible substrate 11.

Note that in this embodiment, both of the wire 12 and the back surface wire 19 are formed by forming a copper plating layer on the flexible substrate 11 and thereafter covering the copper plating layer by a silver plating layer. That is, in this embodiment, as the wire 12 and the back surface wire 19, copper wires to which silver plating is applied are used. However, embodiments are not limited to this, but wires may be formed of a material such as aluminum, for example.

As aforementioned, the wires 12 are formed on each of the unit substrates 10 and are coupled with each other by the LED chips 13 and the bonding wires 14 only in the unit substrate 10.

Meanwhile, the back surface wire 19 is formed across the unit substrates 10.

As illustrated in FIG. 2, the back surface wire 19 includes an anode back surface wire 19a and a cathode back surface wire 19b.

A cathode electrode of the LED chip 13 is connected with the wire 12 on which the LED chip 13 is mounted by the bonding wire 14. Meanwhile, an anode electrode of the LED chip 13 as connected with the wire 12 on which the LED chip 13 is mounted by the other bonding wire 14 than the above bonding wire 14. However, the anode electrode of the LED chip 13 that positioned in one end portion of the wiring pattern 29 is connected with the anode back surface wire 19a by the bonding wire 14 via the front-back wire connection portion 18. Meanwhile, the cathode electrode of the LED chip 13 that is positioned in the other end portion of the wiring pattern 29 is connected with the cathode back surface wire 19b by the bonding wire 14 via the other front-back wire connection portion 18 than the front-back wire connection portion 18 connected with the above anode back surface wire 19a.

As illustrated in FIG. 1 and FIG. 2, each of the unit substrates 10 is provided with a pair of front-back wire connection portions 18 that are correspondent to the one end portion and the other end portion of the wiring pattern 29 in each of the unit substrates 10.

Further, as illustrated in FIG. 2, the external connection portions 21 include an anode external connection portion 21a and a cathode external connection portion 21b.

The external connection portions 21 are provided in one end portion of the light irradiation substrate 1 so that the above anode external connection portion 21a and cathode external connection portion 21b may be extracted from one end side of the light irradiation substrate 1. In this embodiment, the anode external connection portion 21a and the cathode external connection portion 21b are provided in the end portion on the opposite side to the unit substrate 10b in the unit substrate 10a that is positioned in one end portion in the alignment direction of the unit substrates 10a to 10c. Note that the external connection portion 21 will later be described in detail.

The anode back surface wire 19a includes an anode terminal portion 51 and plural power supply lines 52. The anode terminal portion 51 is a connection portion that is connected with the anode external connection portion 21a and is provided in one end portion of the anode back surface wire 19a.

The power supply lines 52 are connected with the anode terminal portion 51 and are arranged in parallel with each other. The power supply lines 52 extend from the connection portion in the anode back surface wire 19a with the anode external connection portion 21a to the respective unit substrates 10 provided with the LED chips 13 to which power is supplied by the power supply lines 52 and are electrically connected with the wires 12 of the respective unit substrates 10.

This embodiment includes power supply lines 52a to 52c as the power supply lines 52. The power supply line 52a is connected with the wire 12 in the unit substrate 10a. The power supply line 52b is connected with the wire 12 in the unit substrate 10b. The power supply line 52c is connected with the wire 12 in the unit substrate 10c. Note that in a case where the power supply lines 52a to 52c do not have to be particularly distinguished, those power supply lines 52a to 52c will generically and simply be referred to as power supply line 52.

Similarly, the cathode back surface wire 19b includes a cathode terminal portion 61 and plural power supply lines 62. The cathode terminal portion 61 is a connection portion that is connected with the cathode external connection portion 21b and is provided in one end portion of the cathode back surface wire 19b.

The power supply lines 62 are connected with the cathode terminal portion 61 and are arranged in parallel with each other. The power supply lines 62 extend from the connection portion in the cathode back surface wire 19b with the cathode external connection portion 21b to the respective unit substrates 10 provided with the LED chips 13 to which power is supplied by the power supply lines 62 and are electrically connected with the wires 12 of the respective unit substrates 10.

This embodiment includes power supply lines 62a to 62c as the power supply lines 62. The power supply line 62a is connected with the wire 12 in the unit substrate 10a. The power supply line 62b is connected with the wire 12 in the unit substrate 10b. The power supply line 62c is connected with the wire 12 in the unit substrate 10c. Note that in a case where the power supply lines 62a to 62c do not have to be particularly distinguished, those power supply lines 62a to 62c will generically and simply be referred to as power supply line 62.

The LED chips 13 are connected in parallel among the unit substrates 10 by such connection of wires. Each of the LED chips 13 is supplied with power via the back surface wire 19 and the wire 12.

The light irradiation substrate 1 causes a front side thereof to be opposed to the affected part and performs light irradiation by connecting the external connection portions 21 to an external power source.

In this embodiment, the back surface wire 19 and the external connection portions 21 are provided on the back surface side of the flexible substrate 11, and inhibition of light irradiation by current supply means to the light irradiation substrate 1 in the treatment may thereby entirely be prevented.

Further, the back surface of the flexible substrate 11 is provided with the power supply lines 52a to 52c and 62a to 62c that extend from the connection portions (that is, the anode terminal portion 51 and the cathode terminal portion 61) with the external connection portions 21 in the back surface wire 19 to the unit substrates 10a to 10c and that are electrically connected with the wires 12 of the unit substrates 10a to 10c as the extension destinations, and those power supply lines 52a to 52d and 62a to 62c are respectively arranged in parallel. Thus, even in a case where the other unit substrates 10 than the unit substrate 10a provided with the external connection portions 21 are cut and separated, the light irradiation substrate 1 is usable as the light irradiation substrate.

The light irradiation substrate 1 may be used by cutting off the light irradiation substrate 1 into a requested size in accordance with the size of the affected part. For the affected part with a small area, only the unit substrate 10a that has the external connection portions 21 may be detached from the other unit substrates 10 and may thereby be used individually. For the affected part with a large area, the light irradiation substrate 1 may be used without cutting. In such a manner, the number of requested unit substrates may be selected in accordance with the size of the affected part.

Note that in case where plural light irradiation substrates 1 are used, a control power source may be prepared which has plural power source units which are not illustrated and may perform parallel control. In this case, the requested number of power source units is the same as the number of light irradiation substrates 1.

Each of the unit substrates 10 has to have substantially the same light irradiation intensity. The variation of the light irradiation intensity of the unit substrates 10 is preferably 10% or less. With this restriction, the irradiation time includes a margin of approximately 10%, and the same irradiation intensity may thereby be realized even in a case of driving at the same current.

In order to keep substantially the same light irradiation intensity of the unit substrates 10, the same current amount has to be supplied to the unit substrates 10. In order to do so, the wire resistances from the external connection portions 21 to the unit substrates 10 have to be substantially the same.

In order to suppress the light irradiation intensity unevenness due to the wire resistances to 1% or less, the differences in the resistance value among the power supply lines 52a to 52c and 62a to 62c are desirably within 20%.

The back surface wire 19 is designed in consideration of this point. In this embodiment, the wire length of each of the power supply lines 52a and 62a is set to 30 mm, the wire length of each of power supply lines 52b and 62bb is set to 70 mm, and the wire length of each of power supply lines 52c and 62bc is set to 110 mm. Thus, the wire width of each of the power supply lines 52a and 62a is set to 2 mm, the wire width of each of the power supply lines 52c and 62bc is set to 4.7 mm, and the wire width of each of the power supply lines 52c and 62bc is set to 7.4 mm.

(External Connection Portion 21)

The external connection portions 21 are wire portions for connecting the light irradiation substrate 1 with the external power source that supplies current to the light irradiation substrate 1.

As illustrated in FIG. 2, in this embodiment, the external connection portions 21 are provided on the back surface side of the flexible substrate 11. Wire connection of the external connection portions 21 with the back surface wire 19 is performed by soldering connection or the like. The back surface wire 19 is joined to a portion of the wire 12 on the front side via the front-back wire connection portion 18, and the external connection portions 21 are electrically connected with the wires 12 via the back surface wire 19.

Note that as described later, a spacer 33 (see FIG. 5) that keeps the distance from the affected part and fixes the positional relationship between the light irradiation substrate 1 and the affected part is provided on a front surface side of the light irradiation substrate 1. Thus, it is difficult to provide the wire connection portion between the back surface wire 19 and the external connection portions 21 on the front surface side of the light irradiation substrate 1.

Further, in a case where the above wire connection portion is provided on the front surface side of the light irradiation substrate 1, after the LED chips 13 are mounted, connecting work (soldering) for the external connection portions 21 is requested on a formation surface of the LED chips 13 and the wires 12. Thus, providing the above wire connection portion on the front surface side of the light irradiation substrate 1 may cause short circuit or the like due to lowering of reflectance due to dirt on surfaces of the wires 12 and placement of dust in gaps among the wires 12 and may lower the production yield of the light irradiation substrate 1.

However, the external connection portions 21 are drawn out to the back surface side of the flexible substrate 11 as described above, the above wire connection portion may thereby be formed easily, and the above-described problems may be avoided.

The external connection portion 21 includes a lead, a connector for connecting the lead with the flexible substrate 11, and so forth, for example. Further, the external connection portion 21 preferably terminates by a socket, a plug, or the like for enhancing convenience of connection with the power source and is preferably formed to easily be connected with the power source.

Figure 4:
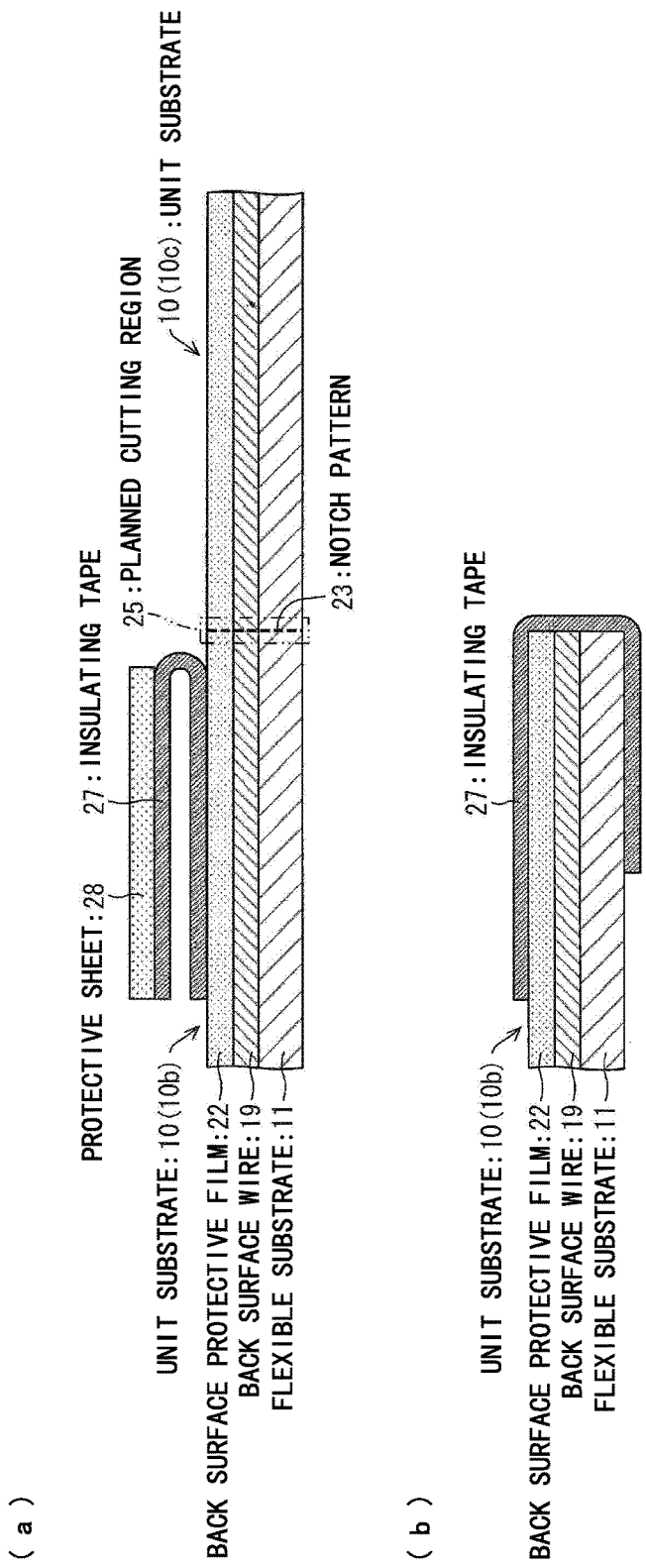
FIGS. 4(*a*) and 4(*b*) are cross-sectional schematic diagrams that illustrate the vicinity of a boundary between the unit substrates of the light irradiation substrate according to the first embodiment of the present invention.

Accordingly, although FIG. 1, FIG. 3, and FIG. 4 illustrate the lead as the external connection portion 21, this is merely an example. It is matter of course that a connector for connecting the lead and so forth may actually be installed in the flexible substrate 11.

Further, as described above, the wire connection portion between the external connection portions 21 and the back surface wire 19 is preferably covered by the connection portion seal that is formed of an insulating resin and is not illustrated. The above wire connection portion is covered by the connection portion seal, the connection portions on an anode side and a cathode side may thereby be insulated and separated from each other, and insulation of the back surface of the light irradiation substrate 1 may be secured.

(LED Chip 13 and Bonding Wire 14)

The LED chip 13 has to be selected in accordance with the purpose of treatment. Here, because the LED chip 13 is applied to "a treatment for skin ulcer infected with methicillin-resistant *Staphylococcus aureus* (MRSA) (see NPL 1)", a gallium-nitride-based bluish violet LED (a peak wavelength of 410 nm) is used for the LED chip 13. As for other uses, as the LED chip 13, the optimal LED may be selected in accordance with the purpose, such as an ultraviolet LED, a blue LED, and a green LED that are similar gallium nitride (AlInGaN) LEDs, red, yellow, and green LEDs of quaternary (AlGaInP) LEDs, a GaAs-based infrared LED, and so forth. Note that as the LED chip 13, it is possible to combine LEDs with different wavelength ranges.

In order to perform uniform light irradiation for the affected part with a specific extent as in phototherapy, it is better to arrange a large number of comparatively small LED chips 13 than to use a small number of LED chips 13 with high power. In this embodiment, as the LED chips 13, 16 bluish violet LED chips with a size of 440 μm×550 μm are mounted on the flexible substrate 11.

As aforementioned, the LED chips 13 are arranged such that the LED chips 13 in each of the unit substrates 10 form the 4×4 two-dimensional array along the X direction and the Y direction as illustrated in FIG. 1 and FIG. 2. As illustrated in FIG. 1, given that the pitch between the LED chips 13 that neighbor each other in the X direction is set as Px and the pitch between the LED chips 13 that neighbor each other in the Y direction which is orthogonal to the X direction is set as Py, the LED chips 13 are arranged at substantially regular intervals (Px, Py) as a two-dimensional array.

Here, the X direction and the Y direction are the alignment directions of the LED chips 13. In this embodiment, the LED chips 13 are aligned in parallel with each side of the rectangular (for example, square) unit substrate 10. Further, the pitch between the LED chips 13 that neighbor each other in the above X direction or Y direction represents the distance between the centers of the LED chips 13 that neighbor each other in the above X direction or Y direction.

In such a manner, the LED chips 13 are arranged in the light irradiation substrate 1 at substantially regular intervals (Px, Py) as a two-dimensional array, and the uniformity of the light irradiation intensity in the light irradiation substrate 1 may thereby be improved.

Note that although Px=Py holds in general, the light output distribution may be different between the above X direction and Y direction depending on the shape of the LED chip 13. In this case, the pitches (Px, Py) between the LED chips 13 may have to be changed in the above X direction and Y direction. For example, the LED chip 13 in a thin and long shape is likely to emit light in the perpendicular direction to the longer side, and less light tends to be emitted in the perpendicular direction to the shorter side. Further, in a case where the longer side of the LED chip 13 is parallel with the above X direction, for example, it is requested that Px<Py holds. In order to most simplify the pitches (Px, Py), the LED chip 13 that is almost a square may be used so that Px=Py holds. Note that the above-described tendency may be influenced by the arrangement of electrodes of the LED chip Thus, optimization has to be made in accordance with the light emission characteristic of the actual LED chip 13.

In this embodiment, the average pitches (Px, Py) of the above LED chip 13 are set to approximately 5 to 10 mm. As the LED chip 13 of this size, an LED chip with the most common structure in which a nitride semiconductor layer epitaxially grown on a sapphire substrate and a cathode electrode and an anode electrode are formed on the same surface has the best luminous efficiency.

In this embodiment, the above-described LED chip 13 in which the cathode electrode and the anode electrode are formed on the same surface is adhered on the wire 12 by a transparent die-bonding paste, and the cathode electrode and the anode electrode of the LED chip 13, which are not illustrated, are connected (wire connection) with the wire 12 by the bonding wires 14 as illustrated in FIG. 1 to FIG. 3.

Gold (gold bonding wire) is used for the bonding wire 14. However, the bonding wire 14 does not have to be gold, but a bonding wire formed of silver, aluminum, or the like in related art may be used.

Note that in the treatment, in a case where the quaternary (AlGaInP) LED or a GaAs infrared LED is used as the LED chip 13, the LED chip 13 has a so-called upper-lower electrode structure. Thus, in a case where the LED chip 13 in which the cathode electrode and the anode electrode are in the upper-lower electrode structure as described above is used, a lower surface of the LED chip as a lower electrode of the LED chip 13 is adhered on the wire 12 by a conductive material such as silver paste, and an upper electrode is connected by the bonding wire 14 with the other wire 12 than the wire 12 on which the LED chip 13 is mounted.

As described above, the uniformity of the light irradiation intensity in each of the unit substrates 10 may be secured by arranging the LED chips 13 as the two-dimensional array (that is, the pitch of the LED chip 13 in the X direction is set as Px, and the pitch in the Y direction is set as Py).

In this embodiment, because the light irradiation substrate 1 has a structure in which the plural unit substrates 10 are joined together, it is important to secure the uniformity of the light irradiation intensity in boundary portions (connection portions) of the unit substrates 10.

The uniformity of the tight irradiation intensity in the boundary portion between the neighboring unit substrates 10 may be secured by keeping the above-described pitches (Px, Py) of the LED chips 13 in each of the unit substrates 10 also between the unit substrates 10.

Accordingly, given that the distance (pitch) between the centers of the LED chips 13 that neighbor each other while facing a boundary between the neighboring unit substrates 10 in the above X direction is set as Dx, it is ideal that Dx=Px holds. However, because Dx includes the planned cutting region 25, a space for cutting has to be secured. Further, in fabrication, in a case where the plural light irradiation substrates 1 are used while being lined up in the X direction, or the like, the unit substrates 10 may have to be connected together, or the plural unit substrates 10 may have to be arranged to be lined up. Thus, it is difficult to strictly maintain the relationship of Dx=Px. Thus, lowering in the irradiation intensity between the unit substrates 10 may have to be accepted to some extent. Accordingly, Dx and Px preferably satisfy the relationship of Dx≤2×Px. Consequently, the lowering in the irradiation intensity in the boundary portion between the neighboring unit substrates 10 in the X direction may be suppressed to 30% or less. The irradiation time is extended 1.4 times longer, and the irradiation with a requested dose amount may thereby be performed.

However, because Dx includes the planned cutting region 25 or a region for connection, Dx may not considerably be reduced compared to Px in fact. Accordingly, Dx desirably satisfies 0.8×Px≤Dx.

Figure 6:
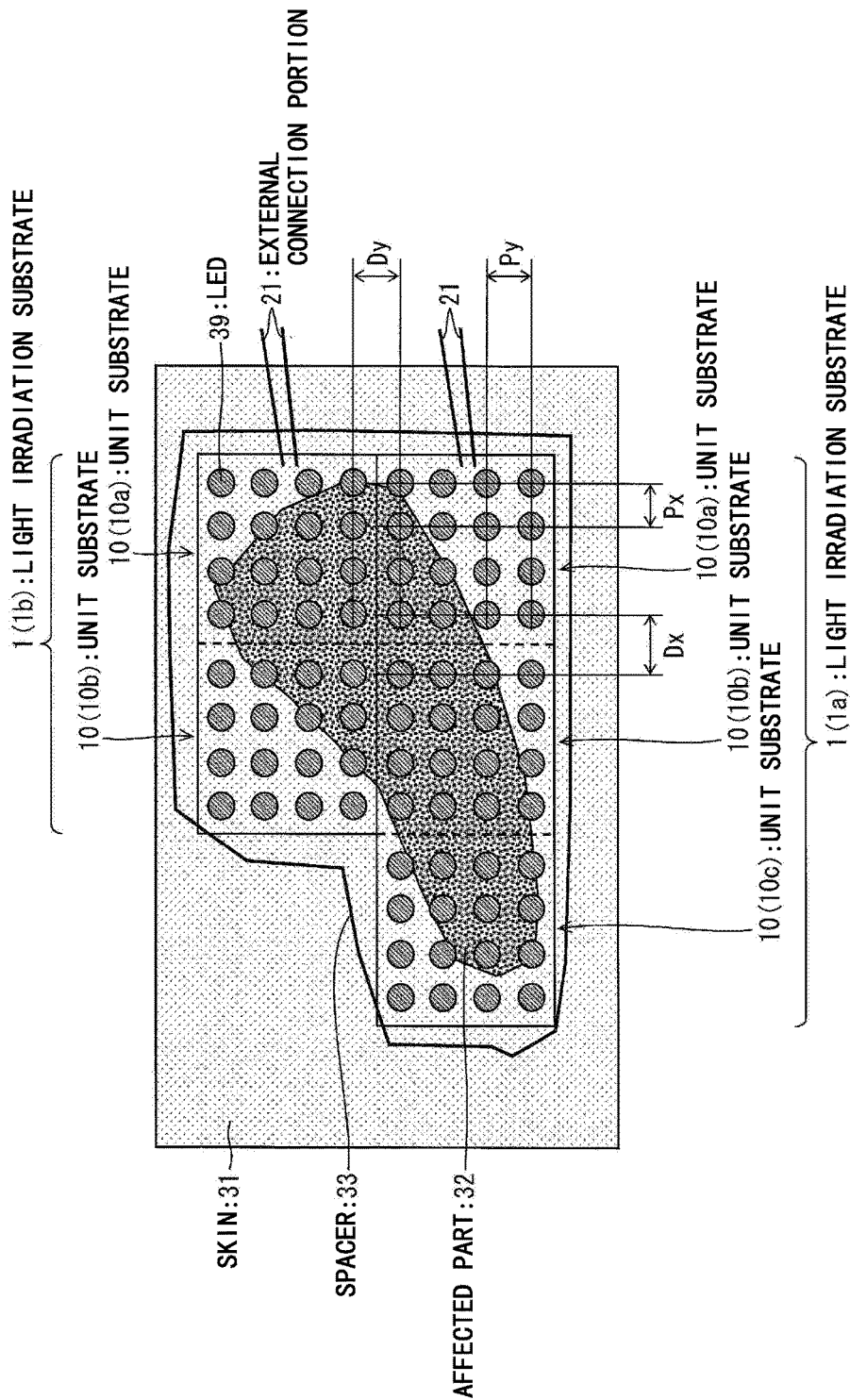
FIG. 6 is a plan schematic diagram that illustrates an application example of the light irradiation substrate according to the first embodiment of the present invention to a treatment.

FIG. 6 is a plan schematic diagram that illustrates an application example of the light irradiation substrate 1 to the treatment. As illustrated in FIG. 6, in a case where the plural light irradiation substrates 1 are provided to be lined up in the Y direction or where the light irradiation substrate is used which has a structure in which the plural light irradiation substrates 1 are joined together in the Y direction, it is important to secure the uniformity of the light irradiation intensity in the boundary portions (connection portions) of the neighboring unit substrates 10 not only in the X direction but also in the Y direction.

Accordingly, as illustrated in FIG. 6, given that the distance (pitch) between the centers of the LED chips 13 that neighbor each other while facing the boundary between the neighboring unit substrates 10 in the Y direction is set as Dy, it is ideal that Dy=Py holds in the Y direction, similarly to the X direction.

However, in a case where the light irradiation substrate has a structure in which the plural light irradiation substrates are joined together in the Y direction, Dy includes a planned cutting region, and a space for cutting thus has to be secured. Further, in fabrication, in a case where the plural light irradiation substrate 1 are used while being lined up in the Y direction, or the like, the unit substrates 10 may have to be connected together, or the plural unit substrates 10 may have to be arranged to be lined up.

Accordingly, for a similar reason to Dx, Dy preferably satisfies the relationship of Dy≤2×Py. Consequently, the lowering in the irradiation intensity in the boundary portion between the neighboring unit substrates 10 in the Y direction may be suppressed to 30% or less. The irradiation time is extended 1.4 times longer, and the irradiation with a requested dose amount may thereby be performed.

Further, similarly to Dx, because Dy includes the planned cutting region or a region for connection, Dy may not considerably be reduced compared to Py in fact. Accordingly, Dy desirably satisfies 0.8×Py≤Dy also.

Further, as described above, in consideration of a case where the plural light irradiation substrates 1 in a strip shape are provided to be lined up in the Y direction, given that the distance between an edge portion of each of the unit substrates 10 in the Y direction (that is, the edge portion in the light irradiation substrate 1 that does not neighbor the unit substrate 10) and the center of the LED chip 13 that faces the edge portion is set as Ey, Ey×2, that is, the double of Ey (Ey=½Dy) is desirably within a range of ±20% of the pitch Py between the LED chips 13 that neighbor each other in the Y direction in each of the unit substrates 10.

Similarly, in consideration of a case where the plural light irradiation substrates 1 in a strip shape are provided to be lined up in the X direction, given that the distance between an edge portion of the light irradiation substrates 1 in the X direction and the center of the LED chip 13 that faces the edge portion is set as Ex, the double of Ex (that is, ½Dx) is desirably within a range of ±20% of the pitch Px between the LED chips 13 that neighbor each other in the X direction in each of the unit substrates 10.

Note that the pitch Dx and the pitch Dy may be the same or different.

In this embodiment, as the flexible substrate 11, a polyimide sheet of 120 mm×40 mm, which has the shape in which three unit substrates 10 of 40 mm-square are lined up in one line, is used.

The LED chip 13 used in this embodiment is almost a square shape, and the difference in the light irradiation intensity between the X direction and the Y direction is approximately 1%. Thus, the pitch Px and the pitch Py of the LED chip 13 in each of the unit substrates 10 are set to Px Py=10 mm. Further, in this embodiment, as illustrated in FIG. 6, the pitch Dx and the pitch Dy between the LED chips 13 that neighbor each other while facing the boundaries between the neighboring unit substrates 10 in the X direction and the Y direction, respectively, are set to Dx=Dy=10 mm.

Note that in this embodiment, as illustrated in FIG. 1, the light irradiation substrate 1 is formed into a strip shape in which the plural unit substrates 10 are aligned in the X direction, the planned cutting region 25 is provided between the neighboring unit substrates 10 in the X direction, and perforations are formed as the notch pattern 23 in the planned cutting region 25.

However, the light irradiation substrate according to this embodiment is not limited to this but may have the shape in which the light irradiation substrates 1 in the strip shape, which have a configuration in which the plural unit substrates 10 are aligned in the X direction, are connected with each other in the Y direction as described above.

For example, as illustrated in FIG. 6, the light irradiation substrate according to this embodiment may have a shape in which light irradiation substrates 1a and 1b in the strip shape, which have the configuration in which the plural unit substrates 10 are aligned in the X direction, are connected with each other in the Y direction. That is, as illustrated in FIG. 6, the light irradiation substrate according to this embodiment may have a configuration in which the unit substrates 10 are aligned two-dimensionally in the X direction and the Y direction and may be in a configuration in which the same number of pairs of the external connection portions 21 (the anode external connection portions 21a and the cathode external connection portions 21b) as the number of the unit substrates 10 aligned in the Y direction are provided to be lined up in the Y direction in, for example, an end portion of the light irradiation substrate in the X direction. Note that in this case, it is desirable that the planned cutting region is provided between the unit substrates 10 in the Y direction so that cutting is facilitated and the perforations are formed in the planned cutting region as a notch pattern.

Further, in this case, the detached light irradiation substrate 1a or 1b may be used as the individual light irradiation substrate 1, and it is possible to use the light irradiation substrates 1a and 1b as one large integrated light irradiation substrate.

In such a manner, the light irradiation substrate according to this embodiment may have a configuration in which a portion of the unit substrates 10 among the plural unit substrates 10 are provided with at least one pair of the external connection portions 21 that supply power from the outside to the LED chips 13 via the wires 12.

Note that in a case where the light irradiation substrate is used in which the unit substrates 10 are aligned two-dimensionally in the X direction and the Y direction as described above, similarly to a case where the plural light irradiation substrates 1 are used, a control power source may be prepared which has plural power source unit which are not illustrated and may perform parallel control. In this case, the same number of power source units as the number of pairs of the external connection portions 21 (that is, the number of the unit substrates 10 aligned in the Y direction) are requested.

Further, in a case where the light irradiation substrate according to this embodiment has a configuration in which the plural light irradiation substrates 1 in the strip shape are coupled together in the X direction or a configuration in which the unit substrates 10 are aligned two-dimensionally in the X direction and the Y direction, the plural external connection portions 21 are provided. Thus, in this case, the external connection portions 21 do not necessarily have to be provided in an end portion of the light irradiation substrate but may be provided in at least one end portion, a central portion, or the like of the light irradiation substrate. However, in order to secure a current path in a case of cutting the light irradiation substrate, the external connection portions 21 to form a pair (that is, the anode external connection portion 21a and the cathode external connection portion 21b) have to be provided in positions that are not detached from each other when the unnecessary unit substrate 10 is detached.

Note that the size of the light irradiation substrate 1 and the number of unit substrates 10 may be optimized as needed in a range of performance of a production device and are not limited to the size.

In this embodiment, as described above, the back surface wire 19 that is connected with the external connection portions 21 and the wires 12 and supplies power from the external connection portions 21 to the LED chips 13 of the unit substrate 10 which is not provided with the external connection portions 21 via the wires 12 is provided on the back surface of the flexible substrate 11 and across the unit substrates 10. Accordingly, even in a case where the other unit substrate 10 than the unit substrate 10a provided with the external connection portions 21 is cut and separated, the light irradiation substrate is usable as the light irradiation substrate and may be used with no change or by cutting into a requested size in accordance with the size of the affected part.

Thus, the light irradiation substrates do not have to be fabricated one by one in a customized manner in order to handle the affected parts that have various shapes and sizes. Further, stocks may be reduced. Further, because the external connection portions 21 do not have to be formed in all the unit substrates 10, the labor for connection with the external power source may be reduced, and the number of external power sources that are requested for connection may also be reduced.

Further, although the unit substrate 10 that is not used occurs by cutting off the unnecessary unit substrate 10, the unit substrate 10 that is cut off is not provided with the external connection portion 21, and size change may thus be performed inexpensively.

(LED Protecting Resin Dome 15, Protective Film 16, Back Surface Protective Film 22)

In order to protect the LED chip 13 and the bonding wires 14, those LED chip 13 and bonding wires 14 are covered by the LED protecting resin dome 15 that is formed with a dome-shaped resin layer.

Although the LED protecting resin dome 15 may be formed by potting, it is better to perform resin molding by using a metal mold in order to secure shape reproducibility.

Further, in order to prevent corrosion of a silver plating layers in the wires 12 and to secure insulation of the front surface of the light irradiation substrate 1, as described above, the protective film 16 that covers the wires 12 is formed as a wire protective film on the front surface of the flexible substrate 11. The protective film 16 is formed on the front surface on the flexible substrate 11, short circuit between the wires 12 may thereby be prevented, and corrosion of silver may also be prevented.

Similarly, in order to prevent corrosion of a silver plating layer in the back surface wire 19 and to secure insulation of the back surface of the light irradiation substrate 1, as described above, the back surface protective film 22 that covers the back surface wire 19 is formed as the wire protective film on the back surface of the flexible substrate 11. The back surface protective film 22 is formed on the back surface on the flexible substrate 11, short circuit between the back surface wires 19 may thereby be prevented, and corrosion of silver may also be prevented.

Note that in order to secure the flexibility of the light irradiation substrate 1 as much as possible, it is better to use as flexible a resin as possible for the LED protecting resin dome 15, the protective film 16, and the back surface protective film 22. A hard resin may lead to wire breaking of the bonding wire 14, the wire 12, or the back surface wire 19 in a case where the light irradiation substrate 1 is bent.

The LED protecting resin dome 15 and the protective film 16 are desirably formed of the same material (insulating resin), but different material may be used. In this embodiment, a silicone resin is coated on the front surface of the flexible substrate 11 so as to cover the wires 12, and the protective film 16 is thereby formed. In addition, the LED chip 13 and the bonding wires 14 are covered by a silicone resin dome.

Further, those LED protecting resin dome 15, protective film 16, and back surface protective film 22 may be formed of the same material (insulating resin), or different material may be used. In this embodiment, the silicone resin is coated on the back surface of the flexible substrate 11 so as to cover the back surface wire 19, and the back surface protective film 22 is thereby formed.

Insulating Tape 27 and Protective Sheet 28)

FIGS. 4(a) and 4(b) are cross-sectional schematic diagrams that illustrate the vicinity of the boundary (planned cutting region 25) between the unit substrates 10 of the light irradiation substrate 1 according to this embodiment. FIG. 4(a) illustrates a cross section of the light irradiation substrate 1 that is not yet cut, and FIG. 4(b) illustrates a cross section of the light irradiation substrate 1 that results from cutting.

In a case where the light irradiation substrate 1 is cut in the planned cutting region 25 as described above, the back surface wire 19 is exposed on the cut section. Note that although it is possible to use the light irradiation substrate 1 in a state where the back surface wire 19 is exposed on the above cut section, it may be assumed that an electric shock accidentally occurs. Thus, it is desirable that cut section of the back surface wire 19 is not exposed to the outside.

Thus, it is desirable that an insulating member that covers the cut section of the back surface wire 19 which is exposed after detachment of the unnecessary unit substrate is provided in the boundary (planned cutting region 25) between the unit substrates 10 or in a peripheral area thereof while facing the boundary between the unit substrates 10.

Accordingly, in the light irradiation substrate 1 according to this embodiment, as the cut cross section insulating portion 26 (see FIG. 2), as illustrated in FIG. 3 and FIG. 4(*a*), the adhesive insulating tape 27 is arranged as the above insulating member in a disposition region of the back surface wire 19 in the boundary between the unit substrates 10. The insulating tape 27 is stuck to the back surface protective film 22 in the cut cross section insulating portion 26 while a portion of the insulating tape 27 is folded. A portion of a sticking surface that is exposed when the insulating tape 27 is folded and that is not stuck to the back surface protective film 22 is protected the protective sheet 28.

Then, as illustrated in FIG. 4(*b*), the protective sheet 28 is peeled off after the light irradiation substrate 1 is cut, the cut section of the back surface wire 19 together with cut sections of the above back surface protective film 22 and flexible substrate 11 is covered by the insulating tape 27, and the cut section of the back surface wire 19 is thereby not exposed in the light irradiation substrate 1 that results from detachment of the unnecessary unit substrate 1.

(Spacer 33)

Figure 5:
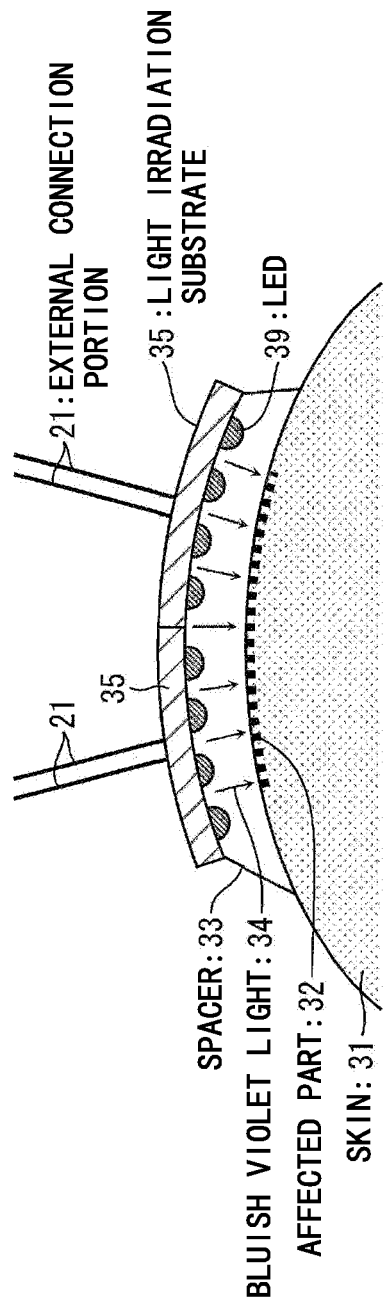
FIG. 5 is a cross-sectional schematic diagram that illustrates an application example of the light irradiation substrate according to the first embodiment of the present invention to a treatment.

FIG. 5 is a cross-sectional schematic diagram that illustrates an application example of the light irradiation substrate 1 according to this embodiment to a treatment.

As illustrated in FIG. 5, in the treatment that uses the light irradiation substrate 1, while the LED 39 is opposed to an affected part 32, light irradiation is performed by connecting the external connection portions 21 to the external power source.

As illustrated in FIG. 5, in light irradiation in the actual treatment, the spacer 33 is requested in order to keep the distance between the front surface of the light irradiation substrate 1 (specifically, surfaces of the LED chips 13) and the affected part 32 and to fix the positional relationship between the light irradiation substrate 1 and the affected part 32, particularly, the positional relationship between the LED chips 13 and the affected part 32.

As the spacer 33, various forms such as a plastic bag that is processed to keep a specific thickness and is filled with water or air, an epoxy-based or polyurethane-based transparent resin plate with flexibility, a water-absorbing polymer that is processed into a plate shape may be used.

The spacer 33 and the light irradiation substrate 1 may be integrated with each other or may be used as separate members.

The spacer 33 may be caused to closely contact with the affected part 32 by thinly applying white petrolatum to the affected part 32 and a periphery thereof, for example. Similarly, the light irradiation substrate 1 and the spacer 33 may be caused to closely contact with each other by thinly applying, for example, the white petrolatum between the light irradiation substrate 1 and the spacer 33.

However, the spacer 33 is in advance adhered on the front surface side of the light irradiation substrate 1, for example, and a step for sticking the light irradiation substrate 1 to the affected part 32 may thereby be facilitated.

Various kinds of adhesives in related art may be used for adhesion between the spacer 33 and the light irradiation substrate 1, for example.

That is, the light irradiation substrate 1 may be a light irradiation substrate with a spacer and may further include, for example, an adhering layer, which is not illustrated, and the above spacer 33 on the LED protecting resin domes 15 and the protective film 16. In other words, the light irradiation substrate with the spacer according to this embodiment may include the light irradiation substrate 1 illustrated in FIG. 1 to FIG. 3, the spacer 33, and the adhering layer that adheres the light irradiation substrate 1 to the spacer 33. Further, an insulating resin is used for each of those LED protecting resin dome 15, protective film 16, and spacer 33, and the light irradiation substrate with the spacer in which the spacer 33 and the light irradiation substrate 1 are integrated without the adhering layer may thereby be obtained.

Note that in light irradiation, sensors such as a temperature sensor and a light intensity sensor are mounted between the spacer 33 and the affected part 32 or skin 31 around the affected part 32, the temperature and the light intensity may respectively be monitored, and the light irradiation power may be controlled by using outputs of those sensors.

Accordingly, sensors such as the temperature sensor and the light intensity sensor may be mounted on the above light irradiation substrate 1 (the light irradiation substrate with the spacer).

Further, in view of making the light irradiation intensity Lo the affected part 32 uniform, the relationship between the thickness of the spacer 33 and the pitches (that is, the pitch Px and the Pitch Py) between the LED chips 13 is important.

Accordingly, given that the average value of the pitches between the neighboring LED chips 13 is set as D and the average thickness of the spacer 33 is set as T, T/D has to satisfy T/D≥0.5 and preferably satisfies T/D≥0.8. In a case where T/D is less than 0.5, the difference in the light irradiation intensity between an immediately lower portion of the LED chip 13 and an immediately lower portion of a central portion between the LED chips 13 becomes approximately twice as large as the light irradiation intensity in the immediately lower portion of the central portion, the light irradiation intensity becomes hugely non-uniform, and this is not preferable.

Note that in this embodiment, for example, as described in an example that will be described later, a resin plate which is an epoxy-based transparent low-viscosity resin "CEP-10A" (product name, NISSIN RESIN Co., Ltd.) formed to have a thickness of about 10 mm and to be at least 10 mm larger than an outer peripheral portion of the affected part 32 is used as the spacer 33, and T/D is set as 10 mm/10 mm=1.0.

Note that in view of the uniformity of the light irradiation intensity, there is not a particular upper limit for the value of T/D. However, as for the easiness of handling in the actual treatment, the handleability is improved as the spacer 33 becomes thinner. Thus, in view of the handleability, the thickness of the spacer 33 is desirably set such that T/D becomes, for example, 2.0 or less.

Further, in view of energy waste in a case where an end portion of the flexible substrate 11 protrudes to the outside of the spacer 33 and of prevention of light irradiation for a normal site, the spacer 33 is desirably formed in the same size as the light irradiation substrate 1 or larger than the light irradiation substrate 1. However, even in a case where the spacer 33 is smaller than the light irradiation substrate 1, the loss significantly low compared to present phototherapy that irradiates the affected part with light all once by a large lamp.

Example 1

In this example, in order to verify the effects of the above light irradiation substrate 1, as illustrated in FIG. 5, an ulcer formed on the back of a pig was caused to be infected with "MRSA", and the light irradiation substrate 1 of this embodiment was applied to phototherapy that used systemic administration of "ALA" and bluish violet light 34 at a wavelength of 410 nm as the treatment light. A portion of "ALA" is converted to "PpIX" in the body of "MRSA". "PpIX" is a photosensitized substance and is decomposed by the bluish violet light 34 as described in NPL 1. It is considered that active oxygen that is generated in the decomposition attacks "MRSA" and "MRSA" may thereby be decreased. The phototherapy is expected as a safe treatment method against antibiotic resistant bacteria.

In this example, two laboratory pigs were prepared, a circular ulcer with a diameter of approximately 20 mm was formed on the back of one pig as sample A, and the ulcer was infected with "MRSA". Further, a long ulcer with a size of approximately 30 mm×105 mm was formed on the back of the other pig as sample B, and the ulcer was infected with "MRSA". "ALA" was in advance administered to both of the pigs, and light irradiation was performed.

Here, for sample A, the unit substrate 10a was detached from the remaining unit substrates 10 by cutting the light irradiation substrate 1 illustrated in FIG. 1, and light irradiation was performed by using the detached unit substrate 10a of 40 mm-square as the light irradiation substrate. Meanwhile, as illustrated in FIG. 6, for sample B, light irradiation was performed by using two light irradiation substrate that were the light irradiation substrate 1a of 80 mm×40 mm which is formed with the three unit substrates 10a to 10c (that is, the light irradiation substrate 1 itself illustrated in FIG. 1) and the light irradiation substrate 1b of 120 mm×40 mm which is formed with the two unit substrates 10a and 10b resulting from detachment of the unit substrate 10c from the light irradiation substrate 1 illustrated in FIG. 1. The transitions in the sizes of ulcers were observed in those states. Note that the pitch of the LED chips 13 was set as Px=Dx=2×Ex=Py=Dy=2×Ey=10 mm.

Further, as described above, as the spacer 33, a resin plate which was the epoxy-based transparent low-viscosity resin "CEP-10A" formed to have a thickness of about 10 mm and to be at least 10 mm larger than the outer peripheral portion of the affected part 32 was used. After this spacer 33 was placed on the affected part 32, the above light irradiation substrate was caused to closely contact onto the spacer 33 while the LED 39 was directed toward the affected part 32. Here, in order to cause the spacer 33 to closely contact with the affected part 32, the white petrolatum was thinly applied to the affected part 32 and a periphery thereof. Note that a similar process was performed between the light irradiation substrate and the spacer 33.

Further, in light irradiation, for sample A, one constant-current power source system that was capable of boosting the voltage to 55 V was used, the constant-current power source was connected with the light irradiation substrate formed only with the unit substrate 10a, and the light irradiation substrate (unit substrate 10a) was driven at a current of 50 mA. Then, a doze amount of 50 J/cm$^2$ was achieved in an irradiation time of 20 minutes while attention was paid to the temperature of the unit substrate 10a.

Meanwhile, for sample B, two constant-current power source systems that were capable of boosting the voltage to 55 V were used, the constant-current power sources were respectively connected with the light irradiation substrates 1a and 1b, and the light irradiation substrates 1a and 1b were driven at a current of 50 mA per unit substrate 10. Note that the light irradiation substrates 1a and 1b were turned ON and OFF at the same timings. Then, a doze amount of 50 J/cm$^2$ was achieved in an irradiation time of 20 minutes while attention was paid to the temperatures of the light irradiation substrates 1a and 1b.

After the above processes were performed, the sizes of the ulcers of the two pigs (samples A and B) were observed. The ulcers of both of them obviously shrank day by day. Because the ulcer as a whole shrank, it may be surmised that an effect of substantially uniformly killing "MRSA" in the entire affected part was present. Based on the above, regardless of the size of tumor, it was found that the light irradiation substrate that used the light irradiation substrate 1 of this embodiment was applied, the phototherapy might thereby be performed, and an effect thereof was present.

Modification Example

Note that in this embodiment, a description is made about a case where the notch pattern 23 for detaching the unnecessary unit substrate 10 is formed in the light irradiation substrate 1, as an example. However, the notch pattern 23 is not necessarily necessary.

In order to enable the unit substrates 10 to be detached from each other, it is sufficient that a space for cutting is provided between the unit substrates 10 and the light irradiation substrate 1 has detachable material, thickness, and so forth.

For example, in this embodiment, it is sufficient that the wiring patterns 29 that are formed with the wires 12 connected by the bonding wires 14 via the LED chips 13 are provided, on the front surface of the above-described flexible substrate 11, to be spaced apart from each other while having the space for cutting.

Further in this embodiment, a description is made about a case where the insulating tape 27 is stuck to the back surface of the light irradiation substrate 1 while facing the planned cutting region 25, as an example. However, the insulating tape 27 is not necessarily stuck to the back surface of the light irradiation substrate 1. A configuration is possible in which the cut section of the back surface wire 19 is protected by using the insulating tape 27 provided separately from the light irradiation substrate 1 after the light irradiation substrate 1 is cut.

Second Embodiment

Another embodiment of the present invention will be described below based on FIG. 7. Note that in this embodiment, different points from the first embodiment will be described. The same reference characters will be given to configuration elements that have the same functions as the configuration elements described in the first embodiment, and a description thereof will not be made.

Figure 7:
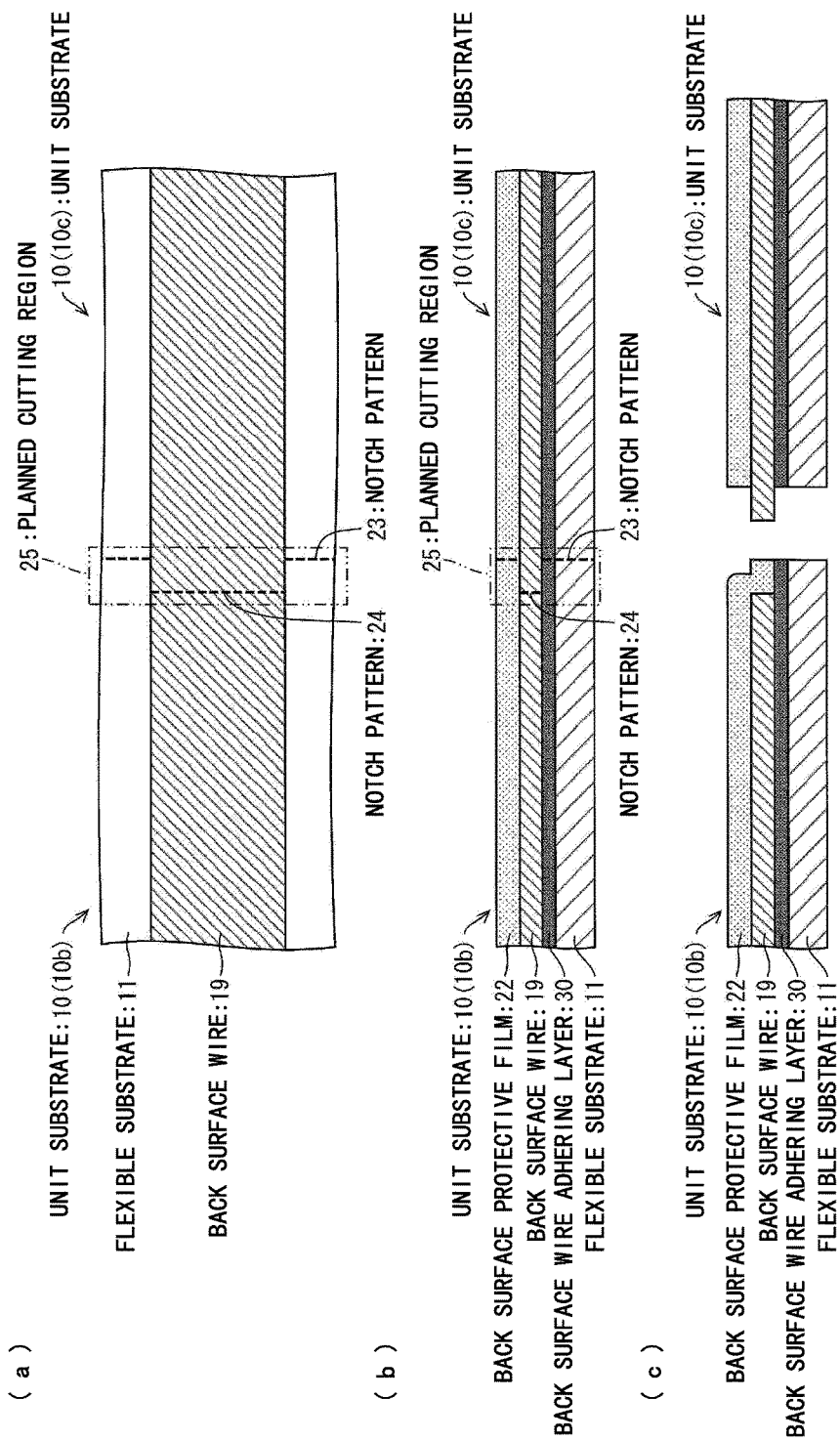
FIG. 7(*a*) is a front surface schematic diagram that illustrates the vicinity of a boundary between the unit substrates of the light irradiation substrate according to a second embodiment of the present invention, and FIGS. 7(*b*) and 7(*c*) are cross-sectional schematic diagrams that illustrate the vicinity of the boundary between the unit substrates of the light irradiation substrate illustrated in FIG. 7(*a*).

FIG. 7(*a*) is a front surface schematic diagram of the vicinity of the boundary (planned cutting region 25) between the unit substrates 10 of the light irradiation substrate 1 according to this embodiment. Further, FIGS. 7(*b*) and 7(*c*) are cross-sectional schematic diagrams that illustrate the vicinity of the boundary between the unit substrates 10 of the light irradiation substrate 1 illustrated in FIG. 7(*a*). FIG. 7(*b*) illustrates a cross section of the light irradiation substrate 1 that is not yet cut, and FIG. 7(*c*) illustrates a cross section that results from cutting of the light irradiation substrate 1. Note that FIG. 7(*c*) does not illustrate the back surface protective film 22 for convenience of illustration.

The light irradiation substrate 1 according to this embodiment has the same configuration as the light irradiation substrate 1 according to the first embodiment except the difference in the structure of the planned cutting region 25.

As aforementioned, it is desirable that the cut section of the back surface wire 19 is not exposed to the outside. Thus, in the first embodiment, the cut section of the back surface wire 19 is covered by the insulating tape 27 that is separately provided from the back surface protective film 22. However, as illustrated in FIG. 7(*c*), this embodiment has a configuration in which the cut section of the back surface wire 19 is positioned on the inside of the cut sections of the above flexible substrate 11 and back surface protective film 22, that is, on the external connection portion 21 side and is thereby covered by the back surface protective film 22.

Specifically, in this embodiment, as illustrated in FIGS. 7(*a*) and 7(*b*), the perforation-like notch pattern 23 (first notch pattern) for cutting the flexible substrate 11 is formed in the boundary between the unit substrates 10, and a perforation-like notch pattern 24 (second notch pattern) for cutting the back surface wire 19 is provided only to the back surface wire 19. Here, the notch pattern 24 is formed on an upstream side (the external connection portion 21 side) of the notch pattern 23 while facing the notch pattern 23.

Further, the back surface wire 19 is laminated on the flexible substrate 11 via a back surface wire adhering layer 30.

Then, a portion in which the notch pattern 24 is formed is folded and further stretched before cutting the flexible substrate 11, the back surface wire 19 is thereby cut, and the remaining portions (flexible substrate 11, back surface wire adhering layer 30, and back surface protective film 22) are thereafter cut.

Consequently, the cut section of the back surface wire 19 is positioned on the inside of the respective cut sections of those flexible substrate 11, back surface wire adhering layer 30, and back surface protective film 22, and the cut section of the back surface wire 19 is covered by the back surface protective film 22. Note that the cut section of the back surface wire adhering layer 30 is positioned on the outside of the cut section of the back surface wire 19, and the back surface protective film 22 is thereby adhered and fixed onto the flexible substrate 11 by the back surface wire adhering layer 30.

In such a manner, in this embodiment, the back surface protective film 22 that covers the back surface wire 19 is used as an insulating member that covers the cut section of the back surface wire 19 which is exposed after detachment of the unnecessary unit substrate 10.

Note that in this case, the notch pattern 23 may be provided only to the flexible substrate 11, the back surface wire adhering layer 30, and the back surface protective film 22 or may be provided to the flexible substrate 11, the back surface wire adhering layer 30, the back surface wire 19, and the back surface protective film 22.

Third Embodiment

Still another embodiment of the present invention will be described below based on FIGS. 8 to 10. Note that in this embodiment, different points from the first embodiment will be described. The same reference characters will be given to configuration elements that have the same functions as the configuration elements described in the first embodiment, and a description thereof will not be made.

Figure 8:
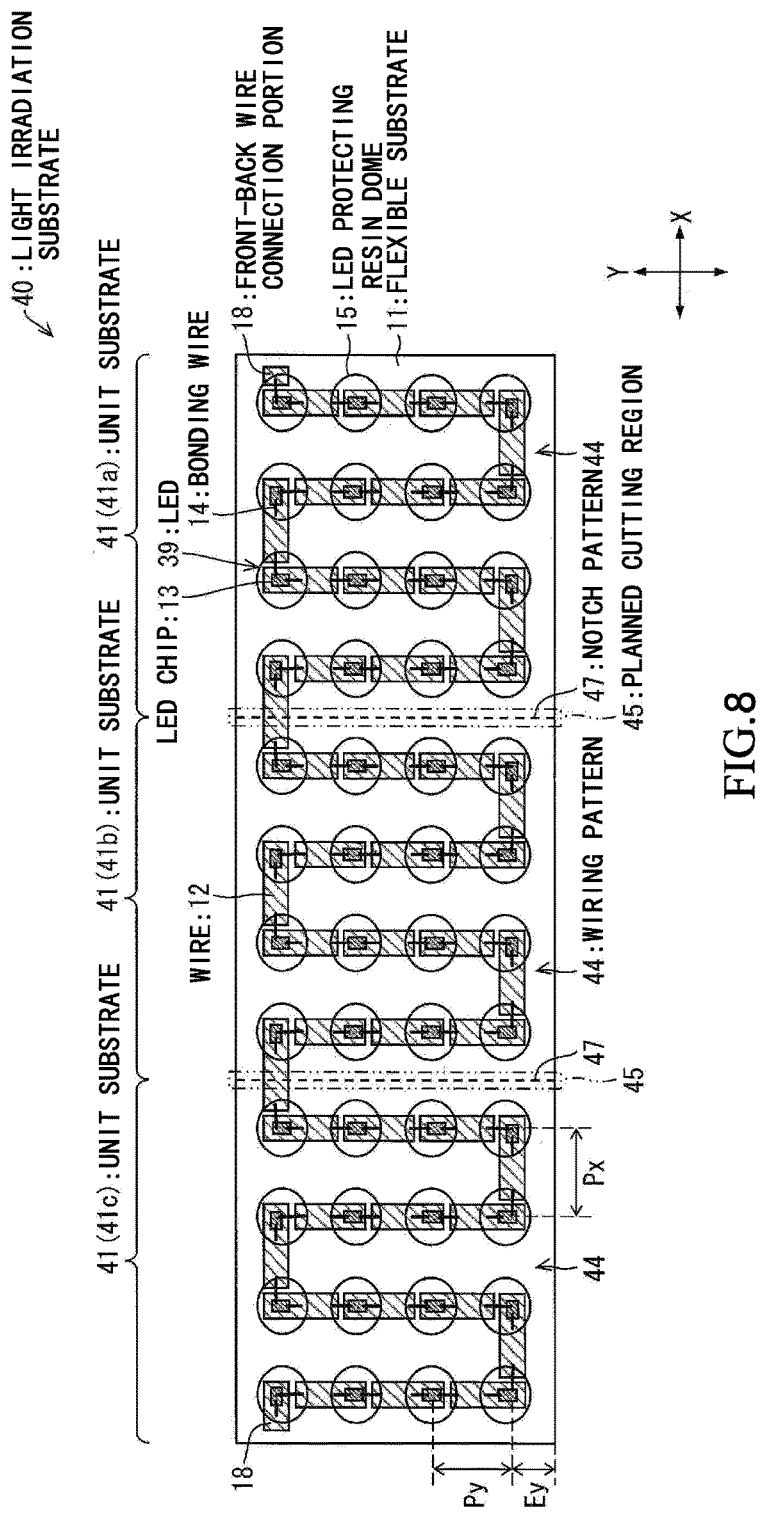
FIG. 8 is a front surface schematic diagram that illustrates a configuration of a light irradiation substrate according to a third embodiment of the present invention.

FIG. 8 is a front surface schematic diagram that illustrates a configuration of a light irradiation substrate 40 according to this embodiment. FIG. 9 is a back surface schematic diagram that illustrates the configuration of the light irradiation substrate 40 according to this embodiment. FIGS. 10(*a*) and 10(*b*) are cross-sectional schematic diagrams that illustrate the vicinity of a boundary between unit substrates 41 of the light irradiation substrate 40 according to this embodiment. FIG. 10(*a*) illustrates a cross section of the light irradiation substrate 40 that is not yet cut, and FIG. 10(*b*) illustrates cross section of the light irradiation substrate 40 that results from cutting.

(Outline Configuration of Light Irradiation Substrate 1)

Figure 9:
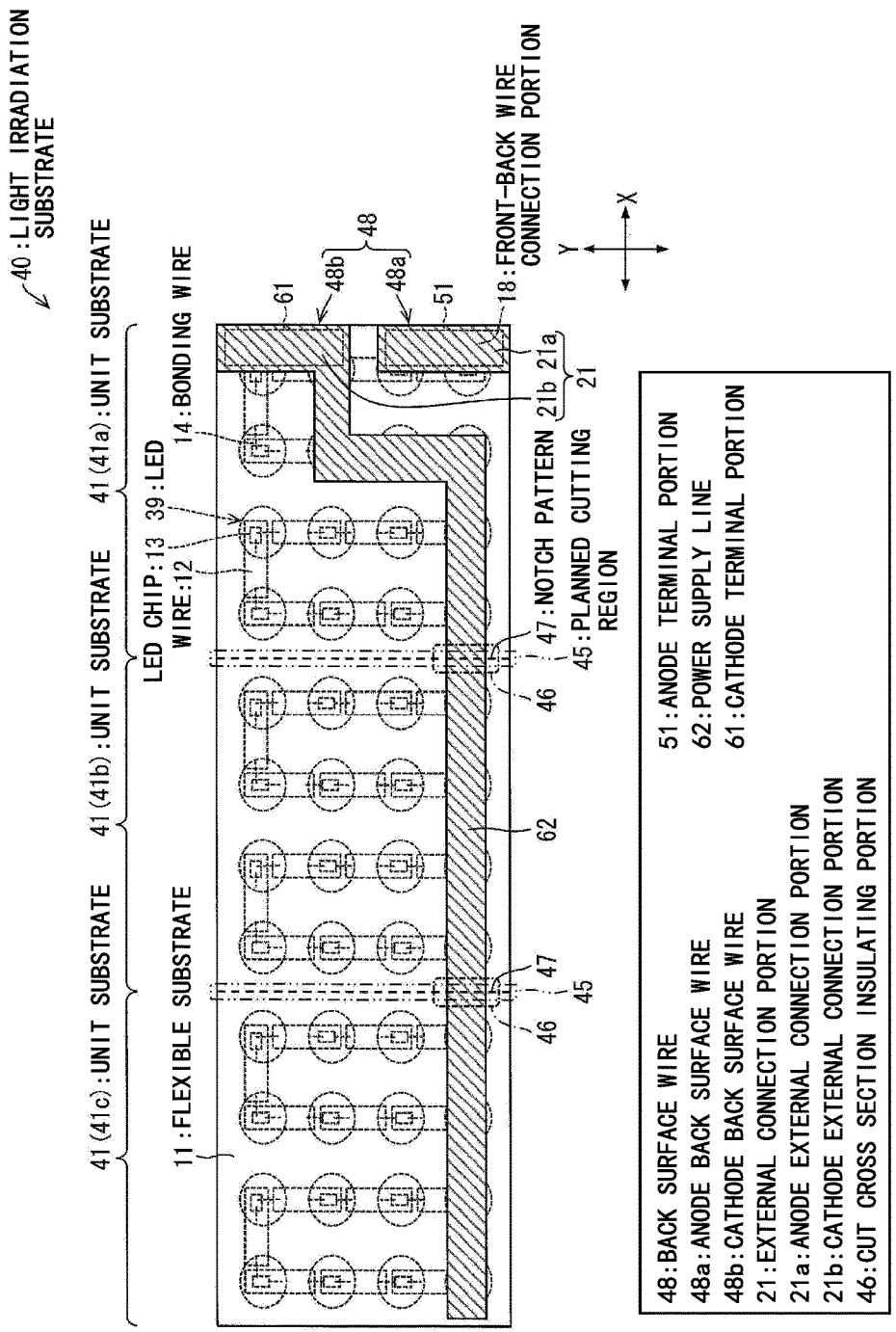
FIG. 9 is a back surface schematic diagram that illustrates the configuration of the light irradiation substrate according to the third embodiment of the present invention.

As illustrated in FIG. 8 and FIG. 9, the light irradiation substrate 40 is configured with plural unit substrates 41 that are mutually detachable.

A boundary portion between the neighboring unit substrates 41 is a planned cutting region 45 for cutting the light irradiation substrate 40. In each of the planned cutting regions 45, a notch pattern 47 for detaching the unit substrate 41 is formed. That is, the unit substrates 10 are connected with each other via the planned cutting region 45.

Figure 10:
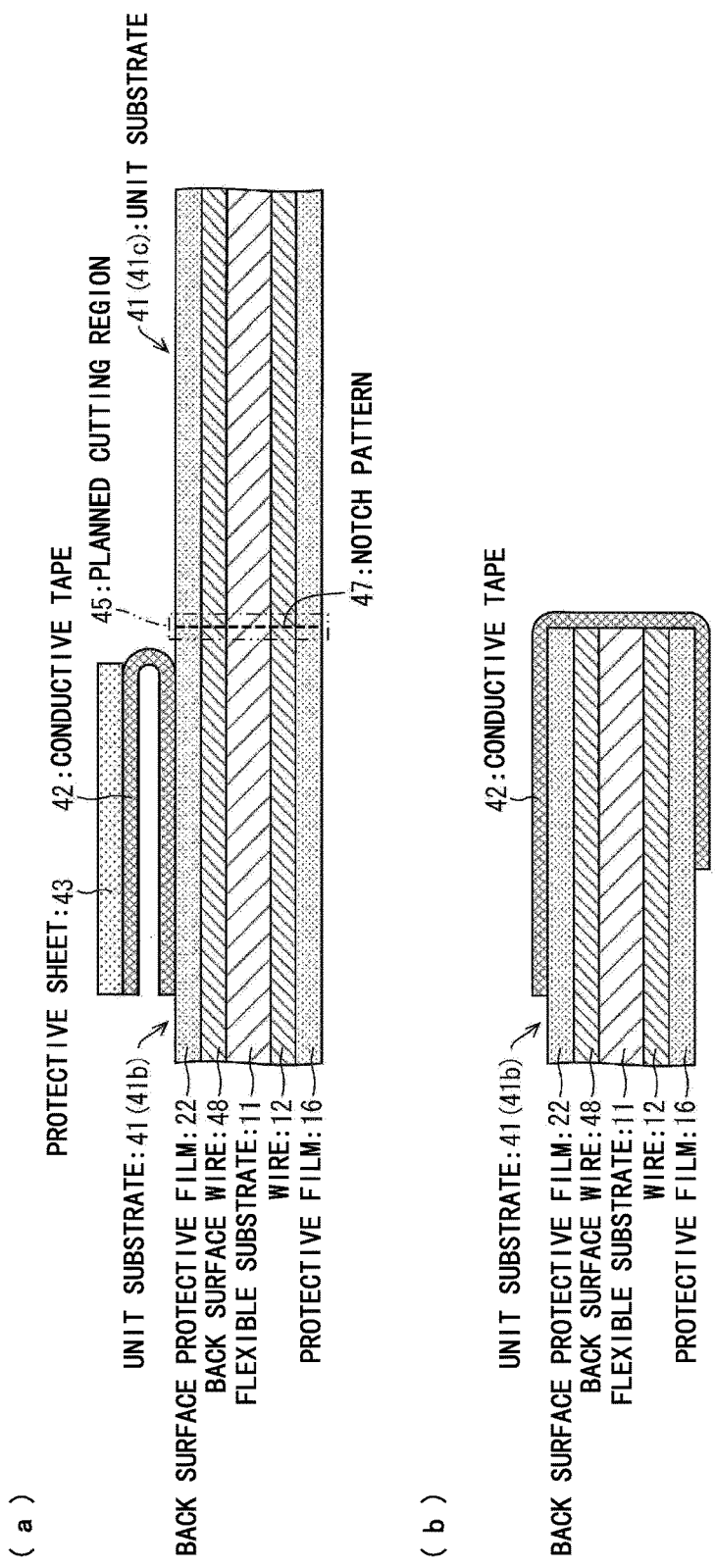
FIGS. 10(*a*) and 10(*b*) are cross-sectional schematic diagrams that illustrate the vicinity of a boundary between unit substrates of the light irradiation substrate according to the third embodiment of the present invention.

Note that FIG. 9 and FIG. 10 illustrate a case where the light irradiation substrate 40 includes three unit substrates 41*a* to 41*c* as the unit substrates 41, as an example. In a case where those unit substrates 41*a* to 41*c* do not have to be particularly distinguished, those unit substrates 41*a* to 41*c* will generically and simply be referred to as unit substrate 41.

The light irradiation substrate 40 includes the flexible substrate 11, the plural wires 12 (first wire), the plural LED chips 13 (light-emitting element), the plural bonding wires 14, the protective film 16, the plural LED protecting resin domes 15, the plural connection holes 17 and front-back wire connection portions 18, a back surface wire 48 (second wire), the external connection portions 21, the back surface protective film 22, plural conductive tapes 42, plural protective sheets 43, and connection portion seals that are not illustrated.

The structures of the light irradiation substrate 40 and the unit substrate 41 are the same as the first embodiment except a wiring pattern by the wires 12 and the back surface wire 48 and the structure of the planned cutting region 45.

The light irradiation substrate 40 is largely different from the first embodiment in a point that the LED chips 13 in all the unit substrates 41*a* to 41*c* are connected in series.

As illustrated in FIG. 8, in the light irradiation substrate 40, the wires 12 of all the unit substrates 41*a* to 41*c* are connected together in one line.

Specifically, the wires 12 in each of the unit substrates 41 are arranged to meander such that the wiring pattern 44 that is formed with the plural wires 12 connected to be lined up in one line by the LED chips 13 and the bonding wires 14 forms a meandering pattern across the unit substrates 41.

Further, as illustrated in FIG. 9, the back surface wire 48 is provided across all the unit substrates 41*a* to 41*c*. The back surface wire 48 is the same as the back surface wire 19 in the light irradiation substrate 1 according to the first embodiment except the following point.

As illustrated in FIG. 9, the back surface wire 48 includes an anode back surface wire 48*a* and a cathode back surface wire 48*b*.

The anode back surface wire 48*a* includes the anode terminal portion 51 and functions as a connection portion that is connected with the anode external connection portion 21*a*.

Meanwhile, the cathode back surface wire 48*b* includes the cathode terminal portion 61 and the power supply line 62.

The cathode terminal portion 61 is a connection portion that is connected with the cathode external connection portion 21*b* and is provided in one end portion of the cathode back surface wire 48*b*.

The power supply line 62 is connected with the cathode terminal portion 61 and extends to the front-back wire connection portion 18 in the unit substrate 41c on the most downstream side from the cathode terminal portion 61. The power supply line 62 is provided across all the unit substrates 41a to 41c.

As illustrated in FIG. 1 and FIG. 2, in an initial state, the unit substrate 41a on the most upstream side that is connected with the external connection portions 21 and the unit substrate 41c on the most downstream side are provided with a pair of respective front-back wire connection portions 18 that are correspondent to one end portion and the other end portion of the wiring pattern 44.

As illustrated in FIG. 8 and FIG. 9, the anode electrode of the LED chip 13 that is positioned in the one end portion of the wiring pattern 44 is connected with the anode terminal portion 51 of the anode back surface wire 48a by the bonding wire 14 via the front-back wire connection portion 18 that is provided in the unit substrate 41a. Meanwhile, the cathode electrode of the LED chip 13 in the other end portion of the above wiring pattern 44 is connected with the cathode back surface wire 48b, which is provided to be stretched from a connection portion with the cathode external connection portion 21b across all the unit substrates 41a to 41c, by the bonding wire 14 via the front-back wire connection portion 18 that is provided in the unit substrate 41c.

In this embodiment, such connection of wires causes all the LED chips 13 in all the unit substrates 41a to 41c to be connected together in series. Each of the LED chips 13 is supplied with power via the back surface wire 48 and the wire 12.

In such a manner, also in this embodiment, similarly to the first embodiment, the back surface wire 48 that is connected with the external connection portions 21 and the wires 12 and supplies power from the external connection portions 21 to the LED chips 13 of the unit substrate 41 which is not provided with the external connection portions 21 via the wires 12 is provided on the back surface of the flexible substrate 11 and across the unit substrates 41. Accordingly, even in a case where the other unit substrate 41 than the unit substrate 41a provided with the external connection portions 21 is cut and separated, the light irradiation substrate is usable as the light irradiation substrate and may be used with no change or by cutting into a requested size in accordance with the size of the affected part. Thus, also in this embodiment, similar effects to the first embodiment may be obtained.

Further, also in this embodiment, the back surface wire 48 and the external connection portions 21 are provided on the back surface side of the flexible substrate 11, and inhibition of light irradiation by current supply means to the light irradiation substrate 1 in the treatment may thereby entirely be prevented.

In addition, in this embodiment, because the same current may be caused to flow through all the LED chips 13, the light irradiation intensity among the unit substrates 41 may be kept the same comparatively easily.

Note that in the above configuration, because the power source voltage becomes high and connection by the conductive tape 42 does not necessarily have a low resistance, the series resistance increases, and a much higher voltage is requested. However, for currents of 100 to 200 mA, it is not difficult to prepare a direct current power source of approximately 150 V, and an advantage of causing the same current to flow through all the LED chips 13 surpasses the difficulty.

(Configuration of Planned Cutting Region 45)

As described above, in the light irradiation substrate 40, the wiring pattern 44 and the back surface wire 48 are provided across all the unit substrates 41a to 41c, and the perforation-like notch pattern 47 is provided to cross the wire 12 and the back surface wire 48 in the planned cutting region 45.

Thus, in this embodiment, in a case of cutting the light irradiation substrate 40, the back surface wire 48 is detached from the wire 12 on the front side.

Thus, as illustrated in FIG. 10(a), in this embodiment, on the back surface protective film 22 on the back surface side of the flexible substrate 11, a conducive member that connects cut sections of the wire 12 and the back surface wire 48 which are exposed after detachment of the unnecessary unit substrate 41 is provided while facing the planned cutting region 45.

Specifically, the adhesive conductive tape 42 is arranged as the above conductive member in a region that faces the back surface wire 48 and the wire 12 in the planned cutting region 45 on the above back surface protective film 22 in a planar view.

The conductive tape 42 is stuck to the back surface protective film 22 while a portion of the conductive tape 42 is folded. A portion of a sticking surface that is exposed when the conductive tape 42 is folded and that is not stuck to the back surface protective film 22 is protected by the protective sheet 43.

Then, as illustrated in FIG. 10(b), the protective sheet 43 is peeled off after the light irradiation substrate 40 is cut, the cut section of the back surface wire 19 is connected with the cut section of the wire 12 by the conductive tape 42, and the current path is thereby secured.

Note that in order to secure the current path, as described above, it is sufficient that a tail end of the wire 12 on the front side of each of the unit substrates 41 that are connected in series is coupled with the back surface wire 48 by the conductive member such as the conductive tape 42 in a case of cutting the light irradiation substrate 40. However, the voltage drop becomes larger as the distance in which current flows through the conductive tape 42 becomes longer, and power consumption increases. Accordingly, in order to suppress such a side effect of the conductive tape 42 to a minimum, the wire 12 on the front side and the back surface wire 48 are desirably positioned in the same position in a planar view in each of the planned cutting regions 45. That is, the tail end of the wire 12 on the front side of each of the unit substrates 41 that are connected in series is desirably arranged to be superimposed on the back surface wire 48 via the flexible substrate 11.

Example 2

A similar experiment to example 1 was conducted in order to verify the effects of the above light irradiation substrate 40. As a result, similar effects to example 1 were confirmed.

Modification Example

Note that in this embodiment, all the LED chips 13 are connected in series. However, in a case where the number of LED chips 13 is large and the power source voltage becomes excessively high only with series connection, or the like, parallel connection may also be used for the connection of the LED chips 13. In such a case, the wiring pattern with the wires 12 and the back surface wire 48 has to be devised such that the same current flows through each of the wires 12.

CONCLUSION

A light irradiation substrate (light irradiation substrate 1 or light irradiation substrate 40) according to a first aspect of the present invention includes plural unit substrates (unit substrates 10 or unit substrates 41) that have the flexible substrate 11 and are mutually detachable, in which a first surface of the flexible substrate 11 has a light-emitting element (LED chip 13) and a first wire (wire 12) for each of the unit substrates, a portion of the unit substrates among the unit substrates have at least one pair of the external connection portions 21 (anode external connection portion 21a and cathode external connection portion 21b) that supply power from an outside to the light-emitting element via the first wire, and a second wire (back surface wire 19 or back surface wire 48) that is connected with the external connection portion 21 and the first wire and supplies power from the external connection portion 21 to the light emitting element of the unit substrate which is not provided with the external connection portion 21 via the first wire is provided on a second surface on an opposite side to the first surface on the flexible substrate 11 and across the unit substrates.

In the above configuration, the light-emitting element provided on the first surface of the flexible substrate 11 is used as a light source, it is possible to perform light irradiation while covering only the affected part, restraint of the patient may thereby be reduced, and the load on the patient may be suppressed to a minimum. Further, the light irradiation substrate may be used for the affected part with a curved surface such as an arm or a leg.

Further, in the above configuration, the back surface wire that is connected with the external connection portions 21 and the wires 12 and supplies power from the external connection portions 21 to the light-emitting elements of the unit substrate which is not provided with the external connection portions 21 via the wires 12 is provided on the second surface of the flexible substrate 11 and across the unit substrates. Accordingly, even in a case where the other unit substrate than the unit substrate (for example, unit substrate 10a or unit substrate 41a) provided with the external connection portions 21 is cut and separated, the light irradiation substrate is usable as the light irradiation substrate and may be used with no change or by cutting into a requested size in accordance with the size of the affected part.

Thus, in the above configuration, the light irradiation substrates do not have to be fabricated one by one in a customized manner in order to handle the affected parts that have various shapes and sizes. It is possible to handle an emergency case, and stocks may be reduced. Further, because the external connection portions 21 do not have to be formed in all the unit substrates, the labor for connection with the external power source may be reduced, and the number of external power sources that are requested for connection may also be reduced.

Further, although the unit substrate that is not used occurs by cutting off the unnecessary unit substrate, the unit substrate that is cut off is not provided with the external connection portion 21, and size change may thus be performed inexpensively.

Accordingly, the above configuration may provide the light irradiation substrate that may suppress costs, handle treatments for diseased parts with various sizes, perform substantially uniform light irradiation for an uneven affected part, suppress side effects by light irradiation to a minimum, realize efficient and uniform light irradiation, and realize phototherapy effects that alleviate loads on the patient and family members.

As for the light irradiation substrate 1 according to a second aspect of the present invention, in the first aspect, the first wire may be independently provided to each of the unit substrates 10, the second wire (back surface wire 19) may have the plural power supply lines 52a to 52c and 62a to 62c that are arranged in parallel with each other, the power supply lines 52a to 52c and 62a to 62c may extend from the connection portion with the external connection portion 21 in the second wire to the unit substrates 10 that are provided with the light-emitting elements to which power is supplied by the power supply lines 52a to 52c and 62a to 62c and may be electrically connected with the first wires of the unit substrates 10, the second wire may connect, in parallel, the light-emitting element that is provided to the unit substrate 10 which is provided with the external connection portion 21 with the light-emitting element that is provided to the unit substrate 10 which is not provided with the external connection portion 21, and differences in resistance values among the power supply lines 52a to 52c and 62a to 62c may be within 20%.

In the above configuration, similar effects to the first aspect may be obtained, the light-emitting elements are connected in parallel, and the power source voltage may thereby be restrained from becoming high even in a case where the number of light-emitting elements is large.

Further, in the above configuration, the wire resistances from the external connection portions 21 to the unit substrates 10 may be made substantially the same, and the light irradiation intensity of each of the unit substrates 10 may be kept substantially the same.

As for the light irradiation substrate 1 according to a third aspect of the present invention, in the second aspect, the wire widths of the power supply lines 52a to 52c and 62a to 62c may be formed wider as the wire lengths become longer.

In order to equalize the resistances of the power supply lines 52a to 52c and 62a to 62c, a method may be used in which the materials of the power supply lines 52a to 52c and 62a to 62c are changed. However, changing wire materials for the wire patterns in such a manner is considerably difficult in reality. Further, copper is usually used as the wire material. For example, using copper and silver with a lower specific resistance than copper separately leads to a cost increase and is thus not realistic.

However, in the above configuration, the resistances of the power supply lines 52a to 52c and 62a to 62c may be equalized inexpensively and easily.

As for the light irradiation substrate 1 according to a fourth aspect of the present invention, in the second or third aspect, the insulating member (insulating tape 27 or back surface protective film 22) that covers the cut section of the second wire (back surface wire 19) which is exposed after detachment of the unnecessary unit substrate 10 may be provided while facing the boundary (planned cutting region 25) between the unit substrates 10.

In a case where the light irradiation substrate 1 is cut in the boundary between the unit substrates 10, the second wire is exposed on the cut section. However, in the above configuration, because the cut section of the second wire is not exposed, there is no risk such as occurrence of an accidental electric shock or the like, and the safe light irradiation substrate 1 may be provided.

As for the light irradiation substrate 1 according to a fifth aspect of the present invention, in the fourth aspect, the insulating member may be the insulating tape 27 in which a portion of the sticking surface is protected by the protective sheet 28.

In the above configuration, the protective sheet 28 is peeled off after the light irradiation substrate 1 is cut, the cut section of the second wire is covered by the insulating tape 27, and the cut section of the second wire may thereby easily be caused not to be exposed in the light irradiation substrate 1 that results from detachment of the unnecessary unit substrate 10.

As for the light irradiation substrate 1 according to a sixth aspect of the present invention, in the fourth aspect, the insulating member may be a protective film (back surface protective film 22) that covers the second wire, the first notch pattern (notch pattern 23) for cutting the flexible substrate 11 may be formed in the boundary between the unit substrates 10 such that the cut section of the second wire that is exposed after detachment of the unnecessary unit substrate 10 is covered by the protective film, and the second notch pattern (notch pattern 24) for cutting the second wire may be formed on the external connection portion 21 side of the first notch pattern while facing the first notch pattern.

In the above configuration, the cut section of the second wire that is exposed after detachment of the unnecessary unit substrate 10 is positioned on the external connection portion 21 side of the cut sections of the flexible substrate 11 and the protective film, and the cut section of the second wire may thereby be covered by the protective film for protection of the second wire without separately providing an insulating member only for covering the cut section of the second wire.

As for the light irradiation substrate 40 according to a seventh aspect of the present invention, in the first aspect, the first wires of all the unit substrates 41 may be connected together in one line, the second wire may be provided across all the unit substrates 41, and the light-emitting elements of all the unit substrates 41 may be connected in series.

In the above configuration, similar effects to the first aspect may be obtained. The light-emitting elements are connected in series, and the same current may thereby be caused to flow through all the light-emitting elements. Thus, the light irradiation intensity among the unit substrates 41 may be kept the same comparatively easily.

As for the light irradiation substrate 40 according to an eighth aspect of the present invention, in the seventh aspect, the first wire and the second wire may be provided to be mutually superimposed in the boundary between the unit substrates 41 via the flexible substrate 11.

In a case where the light-emitting elements are connected in series, the first wire is detached from the second wire by detachment of the unnecessary unit substrate 41. Thus, continuity between the first wire and the second wire is requested. In the above configuration, the continuity between the first wire and the second wire may be obtained with the shortest path. Thus, in securing the current path, the voltage drop may be suppressed to a minimum, and an increase in power consumption may be suppressed.

As for the light irradiation substrate 40 according to a ninth aspect of the present invention, in the seventh or eighth aspect, the conducive member that connects the cut section of the first wire which is exposed after detachment of the unnecessary unit substrate 41 with the cut section of the second wire may be provided while facing the boundary between the unit substrates 41.

In the above configuration, the cut section of the first wire and the cut section of the second wire may be connected together without separately preparing a conductive member and by using the built-in conductive member.

As for the light irradiation substrate 40 according to a tenth aspect of the present invention, in the ninth aspect, the conductive member may be the conductive tape 42 in which a portion of the sticking surface is protected by the protective sheet 43.

In the above configuration, the protective sheet 43 is peeled off after the light irradiation substrate 40 is cut, the cut section of the first wire that is exposed in the boundary between the unit substrates 41 is only connected with the cut section of the second wire by the conductive tape 42, and the current path may thereby easily be secured.

As for the light irradiation substrate (light irradiation substrate 1 or light irradiation substrate 40) according to an eleventh aspect of the present invention, in any one of the first to fifth and seventh to tenth aspects, the notch pattern (notch pattern 23 or notch pattern 47) for detaching the unit substrate may be formed in the boundary between the unit substrates (unit substrates 10 or unit substrates 41).

In the above configuration, the unit substrate may easily be detached.

As for the light irradiation substrate (light irradiation substrate 1 or light irradiation substrate 40) according to a twelfth aspect of the present invention, in any one of the first to eleventh aspects, the external connection portions 21 may be provided in one end portion of the light irradiation substrate.

In the above configuration, the pair of external connection portions 21 may be extracted from one end side of the light irradiation substrate.

As for the light irradiation substrate (light irradiation substrate 1 or light irradiation substrate 40) according to a thirteenth aspect of the present invention, in any one of the first to twelfth aspects, the light-emitting elements of each of the unit substrates (unit substrates 10 or unit substrates 41) may be arranged as a two-dimensional array along a first direction (X direction) and a second direction (Y direction) that is orthogonal to the first direction, and a distance between centers of the light-emitting elements that neighbor each other while facing a boundary between the neighboring unit substrates in the first direction may be in a range that is 0.8 to 2 times as large as a distance between the centers of the light-emitting elements that neighbor each other in the first direction in each of the unit substrates.

In the above configuration, the lowering in the irradiation intensity in the boundary portion between the neighboring unit substrates in the first direction may be suppressed to a specific range. Thus, the light irradiation intensity may be kept substantially uniform in the boundary portion between the unit substrates.

As for the light irradiation substrate (light irradiation substrate 1 or light irradiation substrate 40) according to a fourteenth aspect of the present invention, in any one of the first to the thirteenth aspects, the light-emitting elements of each of the unit substrates (unit substrates 10 or unit substrates 41) may be arranged as a two-dimensional array along the first direction and the second direction that is orthogonal to the first direction, the unit substrates may be aligned only in the first direction, and a double of a distance between an edge portion of the unit substrate in the second direction and the center of the light-emitting element that faces the edge portion may be in a range of ±20% of a distance between the centers of the light-emitting elements that neighbor each other in the second direction in each of the unit substrates.

In the above configuration, even in a case where the plural light irradiation substrates are provided to be lined up in the second direction, the lowering in the irradiation intensity in the boundary portion between the neighboring unit substrates in the second direction may be suppressed to a specific range. Thus, the light irradiation intensity may be kept substantially uniform in the boundary portion between the unit substrates.

The present invention is not limited to the above-described embodiments. Various modifications are possible in the scope described in claims, and embodiments that are obtained by appropriately combining technical means disclosed in the different embodiments are included in the technical scope of the present invention. In addition, new technical features may be formed by combining technical means that are disclosed in the embodiments.

INDUSTRIAL APPLICABILITY

The present invention may preferably be used for a light irradiation substrate that irradiates an affected part of human or animal skin with light.

REFERENCE SIGNS LIST 1, 1a, 1b light irradiation substrate
10, 10a to 10c unit substrate
11 flexible substrate
12 wire
13 LED chip (light-emitting element)
14 bonding wire
15 LED protecting resin dome
16 protective film
17 connection hole
18 front back wire connection portion
19 back surface wire
19a anode back surface wire
19b cathode back surface wire
21 external connection portion
21a anode external connection portion
21b cathode external connection portion
22 back surface protective film (insulating member)
23 notch pattern (first notch pattern)
24 notch pattern (second notch pattern)
25 planned cutting region
26 cut cross section insulating portion
27 insulating tape (insulating member)
28 protective sheet
29 wiring pattern
30 back surface wire adhering layer
31 skin
32 affected part
33 spacer
34 bluish violet light
39 LED
40 light irradiation substrate
41, 41a to 41c unit substrate
42 conductive tape (conductive member)
43 protective sheet
44 wiring pattern
45 planned cutting region
47 notch pattern
48 back surface wire
48a anode back surface wire
48b cathode back surface wire
51 anode terminal portion
52, 52a to 52c, 62, 62a to 62c power supply line
61 cathode terminal portion

The invention claimed is:

1. A light irradiation substrate comprising:
a plurality of unit substrates that have a flexible substrate and are mutually detachable, wherein
each of the unit substrates has a resin covered light-emitting diode configured to emit phototherapeutic light and at least one of first wires on a first surface of the flexible substrate,
one of the unit substrates has at least one pair of external connection portions that is configured to supply power from an outside to the light-emitting diode via the first wires,
second wires that are connected with the external connection portion and the first wires through a thickness of the flexible substrate,
the second wires are configured to supply power from the external connection portion, via the first wires, to the light-emitting element of the unit substrates,
the second wires are arranged on a second surface on an opposite side to the first surface on the flexible substrate and across the unit substrates,
the second wires are configured to electrically connect the unit substrates in parallel with the external connection portion, and
the plurality of unit substrates has a notch pattern which is arranged along a boundary between neighboring unit substrates and through the thickness of the flexible substrate, and is further configured to permit mutual detachment of the unit substrates along the boundary via cutting.

2. A light irradiation substrate comprising:
a plurality of unit substrates that have a flexible substrate and are mutually detachable, wherein
each of the unit substrates has a resin covered light-emitting diode configured to emit phototherapeutic light and at least one of first wires on a first surface of the flexible substrate,
one of the unit substrates has at least one pair of external connection portions that is configured to supply power from an outside to the light-emitting diode via the first wires,
second wires that are connected with the external connection portion and the first wires,
the second wires are configured to supply power from the external connection portion, via the first wires through a thickness of the flexible substrate, to the light-emitting element of the unit substrates,
the second wires are arranged on a second surface on an opposite side to the first surface on the flexible substrate and across the unit substrates,
the first wires are independently arranged to each of the unit substrates,
the second wires have plural power supply lines that are configured to electrically connect the unit substrates in parallel with each other,
at least one of terminal portions of the second wires are connected with the external connection portion,
the plural power supply lines extend from the terminal portions to the unit substrates that are provided with the light-emitting elements to which power is supplied by the power supply lines and are electrically connected with the first wires of the unit substrates,
differences in resistance values among the power supply lines are within 20%, and
the plurality of unit substrates has a notch pattern which is arranged along a boundary between neighboring unit substrates and through the thickness of the flexible substrate, and is further configured to permit mutual detachment of the unit substrates along the boundary via cutting.

3. The light irradiation substrate according to claim 1 or 2, wherein
the first wires of all the unit substrates are connected together in one line, the second wires are arranged across all the unit substrates, and the light-emitting elements of all the unit substrates are connected in series.

4. The light irradiation substrate according to claim 1 or 2, wherein the light-emitting elements of each of the unit substrates are arranged as a two-dimensional array along a first direction and a second direction that is orthogonal to the first direction, and a distance between centers of the light-emitting elements that neighbor each other while facing a boundary between the neighboring unit substrates in the first direction is in a range that is 0.8 to 2 times as large as a distance between the centers of the light-emitting elements that neighbor each other in the first direction in each of the unit substrates.

5. The light irradiation substrate according to claim 1 or 2, wherein the light-emitting elements of each of the unit substrates are arranged as a two-dimensional array along a first direction and a second direction that is orthogonal to the first direction, the unit substrates are aligned only in the first direction, and a double value of a distance between an edge portion of the unit substrates in the second direction and the center of a light-emitting element that faces the edge portion is in a range of ±20% of a distance between the centers of the light-emitting elements that neighbor each other in the second direction in each of the unit substrates.

* * * * *